United States Patent
Macneil et al.

(10) Patent No.: US 12,097,301 B2
(45) Date of Patent: Sep. 24, 2024

(54) SCAFFOLD

(71) Applicant: The University of Sheffield, Sheffield (GB)

(72) Inventors: Sheila Macneil, Sheffield (GB); Christopher Reginald Chapple, Sheffield (GB); Sabiniano Roman Regueros, Sheffield (GB); Christopher James Hillary, Sheffield (GB); Anthony James Bullock, Sheffield (GB)

(73) Assignee: University of Sheffield, Sheffield (GB)

( * ) Notice: Subject to any disclaimer, the term of this patent is extended or adjusted under 35 U.S.C. 154(b) by 1324 days.

(21) Appl. No.: 16/619,256

(22) PCT Filed: Jun. 7, 2018

(86) PCT No.: PCT/GB2018/051557
§ 371 (c)(1),
(2) Date: Dec. 4, 2019

(87) PCT Pub. No.: WO2018/224836
PCT Pub. Date: Dec. 13, 2018

(65) Prior Publication Data
US 2020/0093957 A1 Mar. 26, 2020

(30) Foreign Application Priority Data
Jun. 8, 2017 (GB) ...................... 1709173

(51) Int. Cl.
*A61L 27/18* (2006.01)
*A61F 2/00* (2006.01)
(Continued)

(52) U.S. Cl.
CPC ............ *A61L 27/18* (2013.01); *A61F 2/0036* (2013.01); *A61L 27/3604* (2013.01);
(Continued)

(58) Field of Classification Search
CPC .. A61L 27/18; A61L 27/3604; A61L 27/3834; A61L 27/56; A61L 2430/22;
(Continued)

(56) References Cited

U.S. PATENT DOCUMENTS

2007/0275458 A1* 11/2007 Gouma ................ C12N 5/0068
435/297.4
2010/0233115 A1* 9/2010 Patel ...................... A61L 15/26
425/174.8 E
(Continued)

FOREIGN PATENT DOCUMENTS

CN 105688275 A 6/2016
EP 2921136 A1 9/2015
(Continued)

OTHER PUBLICATIONS

[No Author Listed], WPI Database Submission for CN 105688275. Accession No. 2016-41588N. Clarivate Analytics. 2017:2 pages.
(Continued)

*Primary Examiner* — Sunita Reddy
(74) *Attorney, Agent, or Firm* — Wolf, Greenfield & Sacks, P.C.

(57) ABSTRACT

The present invention relates to a scaffold for the treatment of stress urinary incontinence, wherein the scaffold comprises three layers of polyurethane: a first layer and a third layer in which the polyurethane fibres are randomly orientated and a second layer between said first and third layers in which the fibres are aligned longitudinally; methods of making such scaffolds and uses thereof.

20 Claims, 28 Drawing Sheets

(51) Int. Cl.
  *A61L 27/36* (2006.01)
  *A61L 27/38* (2006.01)
  *A61L 27/56* (2006.01)
  *D01D 5/00* (2006.01)

(52) U.S. Cl.
  CPC ........... *A61L 27/3834* (2013.01); *A61L 27/56* (2013.01); *A61F 2240/001* (2013.01); *A61L 2430/22* (2013.01); *D01D 5/003* (2013.01); *D10B 2331/10* (2013.01); *D10B 2509/00* (2013.01)

(58) Field of Classification Search
  CPC .............. A61F 2/0036; A61F 2240/001; A61F 2/0063; A61F 2/0031; A61F 2/0045; A61F 2002/0068; A61F 2002/047; D01D 5/003; D10B 2331/10; D10B 2509/00
  USPC .......................................... 600/29–30, 36–37
  See application file for complete search history.

(56) References Cited

U.S. PATENT DOCUMENTS

| | | | | |
|---|---|---|---|---|
| 2014/0276997 | A1* | 9/2014 | Harrah | A61F 2/0045 606/151 |
| 2015/0118197 | A1* | 4/2015 | Claeyssens | A61L 27/26 264/401 |
| 2016/0045296 | A1* | 2/2016 | Guo | A61F 2/0063 623/23.74 |
| 2017/0143872 | A1* | 5/2017 | Limem | A61L 27/34 |
| 2018/0296316 | A1* | 10/2018 | Thian | A61F 2/08 |
| 2019/0000602 | A1* | 1/2019 | McCullen | D01D 5/0084 |

FOREIGN PATENT DOCUMENTS

| | | |
|---|---|---|
| WO | WO 2010/042651 A1 | 4/2010 |
| WO | WO 2013/164615 A1 | 11/2013 |
| WO | WO 2015/054677 A1 | 4/2015 |

OTHER PUBLICATIONS

Hillary et al., Developing Repair Materials for Stress Urinary Incontinence to Withstand Dynamic Distension. PLoS One. Mar. 16, 2016;11(3):e0149971.

Roman et al., Evaluating Alternative Materials for the Treatment of Stress Urinary Incontinence and Pelvic Organ Prolapse: A Comparison of the In Vivo Response to Meshes Implanted in Rabbits. J Urol. Jul. 2016;196(1):261-9. Epub Feb. 13, 2016.

Aboushwareb et al., Is tissue engineering and biomaterials the future for lower urinary tract dysfunction (LUTD)/pelvic organ prolapse (POP)? Neurourol Urodyn. Jun. 2011;30(5):775-82. doi: 10.1002/nau.21101.

Badylak et al., Macrophage phenotype as a determinant of biologic scaffold remodeling. Tissue Eng Part A. Nov. 2008; 14(11):1835-42. doi: 10.1089/ten.tea.2007.0264.

Bye et al., Development of bilayer and trilayer nanofibrous/microfibrous scaffolds for regenerative medicine. Biomater Sci. Sep. 30, 20130;1(9):942-951. doi: 10.1039/c3bm60074b. Epub Jun. 3, 2013.

Claerhout et al., Fate of collagen-based implants used in pelvic floor surgery: a 2-year follow-up study in a rabbit model. Am J Obstet Gynecol. Jan. 2008;198(1):94.e1-6. doi: 10.1016/j.ajog.2007.05.032.

Haliloglu et al., The role of urethral hypermobility and intrinsic sphincteric deficiency on the outcome of transobturator tape procedure: a prospective study with 2-year follow-up. Int Urogynecol J. Feb. 2010;21(2):173-8. doi: 10.1007/s00192-009-1010-y. Epub Oct. 3, 2009.

Hong et al., 3D bioprinting and its in vivo applications. J Biomed Mater Res B Appl Biomater. Jan. 2018;106(1):444-459. doi: 10.1002/jbm.b.33826. Epub Jan. 20, 2017.

Kowalczyk et al., Electrospinning of bovine serum albumin. Optimization and the use for production of biosensors. Biomacromolecules. Jul. 2008;9(7):2087-90. doi: 10.1021/bm800421s. Epub Jun. 25, 2008.

Lei et al., Biomechanical properties of prolapsed vaginal tissue in pre- and postmenopausal women. Int Urogynecol J Pelvic Floor Dysfunct. Jun. 2007;18(6):603-7. doi: 10.1007/s00192-006-0214-7. Epub Oct. 6, 2006.

Mangera et al., Are biomechanical properties predictive of the success of prostheses used in stress urinary incontinence and pelvic organ prolapse? A systematic review. Neurourol Urodyn. Jan. 2012;31(1):13-21. doi: 10.1002/nau.21156. Epub Oct. 28, 2011.

Mantovani et al., Macrophage polarization comes of age. Immunity. Oct. 2005;23(4):344-6. doi: 10.1016/j.immuni.2005.10.001.

Toosie et al., Fibrin glue reduces intra-abdominal adhesions to synthetic mesh in a rat ventral hernia model. Am Surg. Jan. 2000;66(1):41-5.

* cited by examiner

SCAFFOLD

RELATED APPLICATIONS

This application is a national stage filing under 35 U.S.C. § 371 of International Patent Application Serial No. PCT/GB2018/051557, filed Jun. 7, 2018, entitled "SCAFFOLD", which claims the benefit of United Kingdom application number GB 1709173.7, filed Jun. 8, 2017, each of which is herein incorporated by reference in its entirety.

FIELD OF THE DISCLOSURE

The present invention relates to scaffolds for the treatment of stress urinary incontinence and methods of making such scaffolds.

BACKGROUND

Stress urinary incontinence (SUI) is a common and debilitating condition that predominantly affects female patients. The condition itself can lead to a significant impact on a sufferer's quality of life and patients often delay seeking treatment, preferring instead to use absorbent pad devices.

In the first instance, SUI is managed with supervised pelvic floor muscle training (PFMT), however, despite this, many patients remain symptomatic and opt to undergo more invasive treatments of their condition. Medications directed specifically at the treatment of SUI, for example duloxetine, are no longer recommended, while drugs aimed to treat co-existing bladder over activity are associated with severe side-effects and may not be effective for pure SUI symptoms. Other minimally invasive treatment options have been investigated, such as the injection of synthetic urethral bulking agents, and while these may be feasible alternatives for patients who are either unfit or unwilling to undergo surgical intervention, the long-term success rates are low.

The surgical treatment of SUI has historically relied upon open abdominal suspension procedures, for example the Burch colposuspension. While this procedure is associated with high cure rates, it was found not to be as effective for SUI that is caused by intrinsic sphincter deficiency (ISD). The artificial urinary sphincter is a successfully used device for the treatment of SUI in male patients and is successfully used in a proportion of women with the more severe form of stress incontinence, ISD. In the female, the inflatable 'cuff' is placed circumferentially around the urethra, with a pump to deflate the cuff tunnelled to the labia, which the woman can operate. Patients are generally very satisfied with these devices, whose fundamental design has changed very little since the 1980's, however the theoretical risk of device infection, erosion and mechanical failure have somewhat limited their widespread use. More recently, autologous fascia slings have been widely used to support the bladder neck and augment urethral closure and these procedures have evolved, with autologous fascia becoming replaced with synthetic materials, such as polypropylene (PP) mesh in the mid-1990s, known as the tension free vaginal tape (TVT). Mesh sling kits are currently marketed, using macrofibrous type I PP mesh (pore size >75 μm). These pre-packaged kits consist of the sling device itself, a sleeve, trocar and introducer set, which are therefore attractive for clinicians to save time and aid placement. However, such PP non-woven meshes repurposed from their use in hernia repair, where they work well, have resulted in severe complications in the treatment of SUI. Complication rate when these are used for stress urinary incontinence is around 10%, but the severity of the symptoms is extreme, and when larger areas are used in pelvic organ prolapse the complication rate may be as high as 30%. Companies supplying these PP meshes are now being sued and have stopped providing the materials.

Accordingly, there is a need for alternative surgical treatments for SUI.

Tissue engineering approaches can develop materials for pelvic floor repair. The "ideal" repair material should remain relatively elastic to cope with the forces experienced with routine events such as coughing or sneezing, but become reversibly stronger at higher strain, similar to native healthy fascia (Mangera et al. 2012). Any materials for load-bearing must have adequate mechanical properties to fulfill a supportive role of the weakened tissue in addition to being biocompatible. Furthermore, materials should be biocompatible and reflect the properties of the tissues into which it is implanted (Aboushwareb et al. 2011). When producing tissue engineered materials, cells must be able to penetrate and populate the material, allowing effective remodelling of tissue. Biodegradable materials ideally undergo controlled degradation over a period that permits tissue remodelling (an M2 macrophage response) with fibroblast ingrowth, ECM production, and angiogenesis (Badylak et al. 2008). Non-degradable materials that result in an acute inflammatory response, persisting to a chronic phase (M1 macrophage response) may be associated with infection and erosion (Mantovani et al. 2005), while materials that fail to initiate an M2 response can become encapsulated (Claerhout et al. 2008).

Polyurethane (PU) materials demonstrate greater elasticity and biocompatibility than PP when used in abdominal hernia repair (Badylak et al. 2008). Previously, the inventors have investigated single layer polyurethane meshes as repair material slings for the treatment of stress urinary incontinence (Hillary et al. 2016). They investigated a single layer of polyurethane, poly-L-lactic acid (PLA) and combinations as scaffolds, as PLA is known to show good cell attachment and matrix production in vitro. PU scaffolds showed good dynamic strain properties, however showed reduced cellular interaction properties and cell penetration when compared to PLA scaffolds. PLA scaffolds, however, lacked the mechanical properties to be suitable for load bearing. Scaffolds of PU containing PLA were weaker and stiffer than PU or PP, but were significantly better than PU scaffolds alone at supporting cell attachment and growth. However, the properties were still sub-optimal.

The inventors have also demonstrated that in a 90 day implantation animal model single layer PU and PLA materials maintain mechanical integrity, and do not show a degree of sustained inflammation when compared to 2 commercially available surgical mesh devices. Good tissue integration was observed of both materials (Roman et al. 2016).

Therefore, there remains a need to find scaffolds with suitable properties to act as alternative surgical treatments for SUI. The scaffolds previously explored lack the properties to successfully mimic the natural fascia.

The inventors also explored multi-layered scaffolds, producing bilayer and tri-layer nanofibrous/microfibrous scaffolds of polyhydroxybutyrate-co-hydroxyvalerate (PHBV), PLA and poly ε-caprolactone (PCL) (Bye et al. 2013). These have potential for tissue regeneration in areas where one wishes to support both soft and hard tissues but keep them separated.

However, the cells in the nano scaffolds showed poor penetration, demonstrating a suitability where the user would wish to keep cells separated, to form distinct tissue types, but not suitability for stress urinary incontinence applications.

BRIEF SUMMARY OF THE DISCLOSURE

The present invention has surprisingly provided a scaffold suitable for the treatment of stress urinary incontinence which has sought to provide the following: viscoelastic properties similar to native tissue fascia, resistance to delamination and penetration of cells through the mesh for successful integration in the patient.

In a first aspect, the present invention relates to a scaffold for the treatment of stress urinary incontinence, wherein the scaffold comprises three layers of polymer which can be biodegradable (as in PLA) or non-degradable (as in polyurethane): a first layer and a third layer in which the fibres are randomly orientated and a second layer between said first and third layers in which the fibres are aligned longitudinally.

Suitably, the polyurethane may be Z3.

Suitably, the scaffold may have an ultimate tensile strength of between 0.25 and 1.5 MPa.

Suitably, the scaffold may have a strain at ultimate tensile strength of between 70% and 80%.

Suitably, the first and third layers of polyurethane comprise pores from the outermost surface of a depth of at least 8 μm suitable for penetration by human adipose derived mesenchymal stem cells.

Suitably, the mean pore size in the first and/or third layer may be at least 10 μm.

Suitably, at least 20% of the pores on the outer surface of the first and/or third layer may be greater than 18 μm.

Suitably, at least 5% of the pores on the outer surface of the first and/or third layer may be greater than 20 μm.

Suitably, scaffolds may have a width of about 1 cm and/or may have a length of about 10 cm.

In another aspect, the present invention provides a method of preparing a scaffold for treatment of stress urinary incontinence, the method comprising:
 a. Electrospinning a sacrificial layer of poly-L-lactic acid onto a rotating surface;
 b. Electrospinning a first layer of polyurethane in which the fibres are spun in random orientations;
 c. Electrospinning a second layer polyurethane in which the fibres are spun in aligned longitudinal orientation;
 d. Electrospinning a third layer in which the fibres are spun in random orientations; and
 e. Removing the sacrificial layer of poly-L-lactic acid to produce the scaffold.

Suitably, the method may comprise the use of at least two separate syringe pumps, one delivering random fibres and one delivering aligned fibres.

Suitably, step c may start before step b finishes such that there is an overlap between the first and second layer.

Suitably, step d may start before step c finishes such that there is an overlap between the second and third layer.

Suitably, the sacrificial layer may be applied to a surface rotating from about 200 to 400 rpm.

Suitably, the sacrificial layer may be produced with a needle to surface distance of from about 12 cm to 17 cm.

Suitably, the sacrificial layer may be produced by delivering polymer solutions at a rate of from about 30 μl/min to 40 μl/min per syringe with an accelerating voltage of from about 15 kV to 19 kV DC.

Suitably, step b may be conducted after any excess solvent from step a. has evaporated.

Suitably, the first and/or third layers may be applied to a surface rotating from about 200 to 400 rpm.

Suitably, the first and/or third layers may be produced with a needle to surface distance of from about 17 to 23 cm and/or the second layer is produced by a needle to surface distance of from about 5 cm to 10 cm.

Suitably, the first and/or third layer may be produced by delivering polymer solutions at a rate of from about 30 μl/min per syringe to 40 μl/min per syringe with an accelerating voltage of from about 17 kV DC to 23 kV DC.

Suitably, the second layer may be applied to a surface rotating from about 500 to 700 rpm.

Suitably, the second layer may be produced by delivering polymer solutions at a rate of from about 30 μl/min per syringe to 40 μl/min per syringe with a voltage of from about 21 kV DC to 25 kV DC.

In a further aspect, the present invention relates to a scaffold produced by the method of the present invention. Suitably, the scaffold may have the properties of a scaffold as disclosed herein.

In another aspect, the present invention provides a scaffold of the present invention or produced by a method of the invention for use as a medicament.

In further aspect, the present invention provides a scaffold of the present invention or produced by a method of the invention use in the treatment of stress urinary incontinence.

Throughout the description and claims of this specification, the words "comprise" and "contain" and variations of them mean "including but not limited to", and they are not intended to (and do not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Various aspects of the invention are described in further detail below.

BRIEF DESCRIPTION OF THE DRAWINGS

Embodiments of the invention are further described hereinafter with reference to the accompanying drawings, in which.

DETAILED DESCRIPTION

Figure 1:
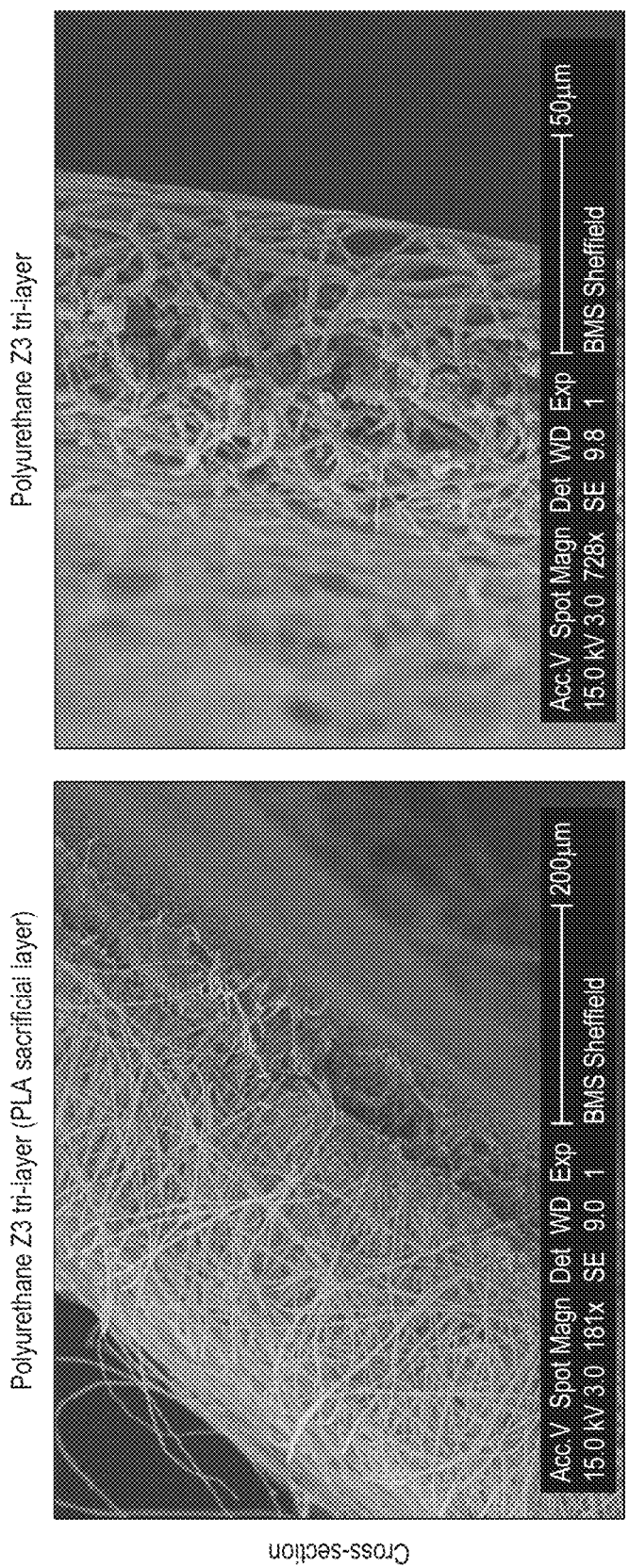
FIG. 1 shows scanning electron microscopy images in cross section to demonstrate the bottom surface of polyurethane scaffolds. These show a 'warped' polymer fibre morphology on the bottom surface of the polyurethane tri-layer scaffold without the presence of a sacrificial layer of PLA.

In a first aspect, the present invention relates to a scaffold for the treatment of stress urinary incontinence, wherein the scaffold comprises three layers of polyurethane: a first layer and a third layer in which the polyurethane fibres are randomly orientated (i.e. spun) and a second layer between said first and third layers in which the fibres are aligned longitudinally.

The term "scaffold", as used herein, refers to any material that allows attachment of cells, preferably attachment of cells involved in wound healing. "Attachment", "attach" or "attaches" as used herein, refers to cells that adhere directly or indirectly to a substrate as well as to cells that adhere to other cells.

The terms "electrospinning" or "electrospun," as used herein to refer to any method where materials are streamed, sprayed, sputtered, dripped, or otherwise transported in the presence of an electric field. The electrospun material can be deposited from the direction of a charged container towards a grounded target, or from a grounded container in the direction of a charged target. In particular, the term "electrospinning" means a process in which fibres are formed from a charged solution comprising at least one natural biological material, at least one synthetic polymer material, or a combination thereof by streaming the electrically charged solution through an opening or orifice towards a grounded target.

As used herein, the terms "solution" and "fluid" refers to a liquid that is capable of being charged and which comprises at least one natural material, at least one synthetic polymer, or a combination thereof. The polymer may be a co-polymer. The term "co-polymer" as used herein is intended to encompass co-polymers, ter-polymers, and higher order multiple polymer compositions formed by block, graph or random combination of polymeric components.

Suitably, the present invention relates to a scaffold for the treatment of stress urinary incontinence, wherein the scaffold may comprise three layers of electrospun polyurethane: a first layer and a third layer in which the polyurethane fibres are randomly spun and a second layer between said first and third layers in which the fibres are aligned longitudinally.

The term "orientated" is used herein to refer to the arrangement of the polyurethane fibres one relative to another within each polyurethane layer. Orientated is used herein interchangeably with "spun". In the scaffold of the present invention, the scaffold comprises three layers of a polymer which is polyurethane. Polyurethane is a polymer composed of organic units joined by carbamate (urethane) links. Polyurethanes may be classified as reaction polymers.

Polyurethanes may be produced by reacting an isocyanate containing two or more isocyanate groups per molecule (R—(N=C=O)$_n$[16]) with a polyol containing on average two or more hydroxyl groups per molecule (R'—(OH)$_n$[16]) in the presence of a catalyst or by activation with ultraviolet light. They can be formulated to be long changed with low crosslinking to give stretchy, flexible polymers, or with short chains and high cross linking, to give hard polymers. They can also be formulated to be foams.

Suitably, the polyurethane may be any medical grade polyurethane. Suitably, the polyurethane may be derived from any medical grade polyether and/or polycarbonate material. Suitably, the polyurethane may be Z3. Polyurethane Z3 is a commercially available medical grade polyurethane (such as from Biomer Technologies (Cheshire)). Advantageously, when polyurethane Z3 is used the scaffold of the present invention may advantageously provide a scaffold which has viscoelastic properties similar to natural fascia. Other polyurethanes having viscoelastic properties similar to polyurethane Z3 may be used in accordance with the present invention. "Viscoelastic properties" may be measured by any one of the following: Young's modulus (e.g. in MPa); ultimate tensile strength (e.g. in MPa) or as a percentage strain at ultimate tensile strength. Other polyurethanes having similar viscoelastic properties to Z3 are known to a person of ordinary skill in the art including, for example: polyether and polycarbonate based medical grade material from DSM Biomedical Inc. (Chemelot Gate 2 (loge Campus), Urmonderbaan 22, 6167 RD GELEEN, The Netherlands), Lubrizol LifeSciences (Chaussée De Wavre, 1945, Brussels, B-1160, Belgium) and AdvanSource Biomaterials (229 Andover St, Wilmington, MA 01887, United States of America). All these polyether and polycarbonate based medical grade materials are designed for biomedical applications with a similar hardness grade to Z3.

Suitably, the scaffold may have an ultimate tensile strength of between 0.25 and 1.5 MPa, preferably about 1 Mpa.

Suitably, the scaffold may have a strain at an ultimate tensile strength of between 70% and 80%, preferably about 70%.

Suitably the scaffold may have a strain at an ultimate tensile strength which is similar to native fascia (e.g. within 10% of the ultimate tensile strength of native fascia).

Suitably, the scaffold may have a Young's modulus of less than 10 MPa, such as in the range of 3 to 10 MPa. Suitably, the scaffold may have a Young's modulus similar to that of native fascia.

Suitably, the first and/or third layers of polyurethane comprise pores from the outermost surface of a depth of at least 8 μm suitable for penetration by human adipose derived mesenchymal stem cells. It is desirable for the scaffold to allow for penetration by human adipose derived mesenchymal stem cells to aid the initial healing phase following implantation of the scaffold and to reduce the inflammatory response to the scaffold.

Suitably, the first and/or third layers of polyurethane comprise pores suitable for penetration by human adipose derived mesenchymal stem cells, wherein the pores from the outermost surface have a depth of at least 8 μm or least 10 μm or at least 12 μm or at least 14 μm or at least 16 μm.

Suitably, the first and/or third layers of polyurethane comprise pores suitable for penetration by human adipose derived mesenchymal stem cells, wherein the pores from the outermost surface have a depth of about 8 μm to 20 μm or about 10 μm to 18 μm or about 14 μm to 16 μm.

Suitably, the first and/or third layers of polyurethane comprise pores suitable for penetration by human adipose derived mesenchymal stem cells, wherein the pores from the outermost surface have a depth of about 16 μm.

Suitably, the depth of the first and/or third layers may be in the range of about 20 μm to 50 μm. Suitably, the first and/or third layers of polyurethane comprise pores suitable for penetration by human adipose derived mesenchymal stem cells of at least 50% of the depth of the layer or at least 60% or at least 70% or at least 80% or at least 90%.

Suitably, at least 20% of the pores on the outer surface of the first and/or third layer may be greater than 18 μm in diameter. Suitably at least 30% or at least 40% or at least 50% of the pores on the outer surface of the first and/or third layer may be greater than 18 μm in diameter. Suitably, about 55% of the pores on the outer surface of the first and/or third layer may be greater than 18 μm in diameter.

Suitably, at least 5% of the pores on the outer surface of the first and/or third layer may be greater than 20 μm. Suitably at least 10% or at least 15% or at least 20% or at least 25% or at least 30% of the pores on the outer surface of the first and/or third layer may be greater than 20 μm in diameter. Suitably, about 30% of the pores on the outer surface of the first and/or third layer may be greater than 20 μm in diameter.

Suitably, scaffold may have a width of about 1 cm and/or may have a length of about 10 cm. However, a skilled person would readily understand that any dimensions which render the scaffold suitable for the intended purpose could be used.

For example, for use in stress urinary incontinence dimensions of up to 10 cm width and 30 cm length may also be applicable for the desired purpose.

Suitably, the scaffold may be prepared in the form of a tape, sheet or reel.

In another aspect, the present invention provides a method of preparing a scaffold for treatment of stress urinary incontinence, the method comprising:

a. Electrospinning a sacrificial layer of poly-L-lactic acid onto a rotating surface;
b. Electrospinning a first layer of polyurethane in which the fibres are spun in random orientations;
c. Electrospinning a second layer polyurethane in which the fibres are spun in aligned longitudinal orientation;
d. Electrospinning a third layer in which the fibres are spun in random orientations; and
e. Removing the sacrificial layer of poly-L-lactic acid to produce the scaffold.

Poly-L-lactic acid is a biodegradable aliphatic polyester, typically formed from natural sources such as corn starch. In production, two main monomers are typically utilised; lactic acid, and the cyclic di-ester, lactide. The most common route to PLA is the ring-opening polymerization of lactide with various metal catalysts (typically tin octoate) in solution, in the melt, or as a suspension. Alternative, lactic acid monomers can be directly condensed together. Polylactic acid is chiral, and several distinct forms can exist; poly-L-lactide (PLLA) is the product resulting from polymerization of L,L-lactide (also known as L-lactide). Polymerization of a racemic mixture of L- and D-lactides usually leads to the synthesis of poly-DL-lactide (PDLLA), which is amorphous. The ring-opening polymerization of lactide with various metal catalysts in solution typically leads to a racemic mix of isomers. Use of stereospecific catalysts can lead to heterotactic PLA which has been found to show crystallinity, largely controlled by the ratio of D to L enantiomers used, and to a lesser extent on the type of catalyst used.

Suitably, the method may comprise the use of at least two separate syringe pumps, one delivering random fibres and one delivering aligned fibres. The method may comprise a plurality of syringes for delivering the random fibres and/or a plurality of syringes for delivering aligned fibres.

The number of needles to be utilised may depend in part of the size of the scaffold to be produced.

Suitably, step c. may start before step b. finishes such that there is an overlap between the first and second layer. Advantageously, by starting step c. prior to finishing step b., the scaffold may have increased resistance to delamination between the first and second layers.

Suitably, step d. may start before step c. finishes such that there is an overlap between the second and third layer. Advantageously, by starting step d. prior to finishing step c., the scaffold may have increased resistance to delamination between the first and second layers.

Whilst in the methods of the present invention it is preferable that there is some overlap between steps b. and c. and some overlap between steps c. and d. these steps do not fully overlap so that three layers are clearly distinguishable in the cross-section of the scaffold.

Figure 5:
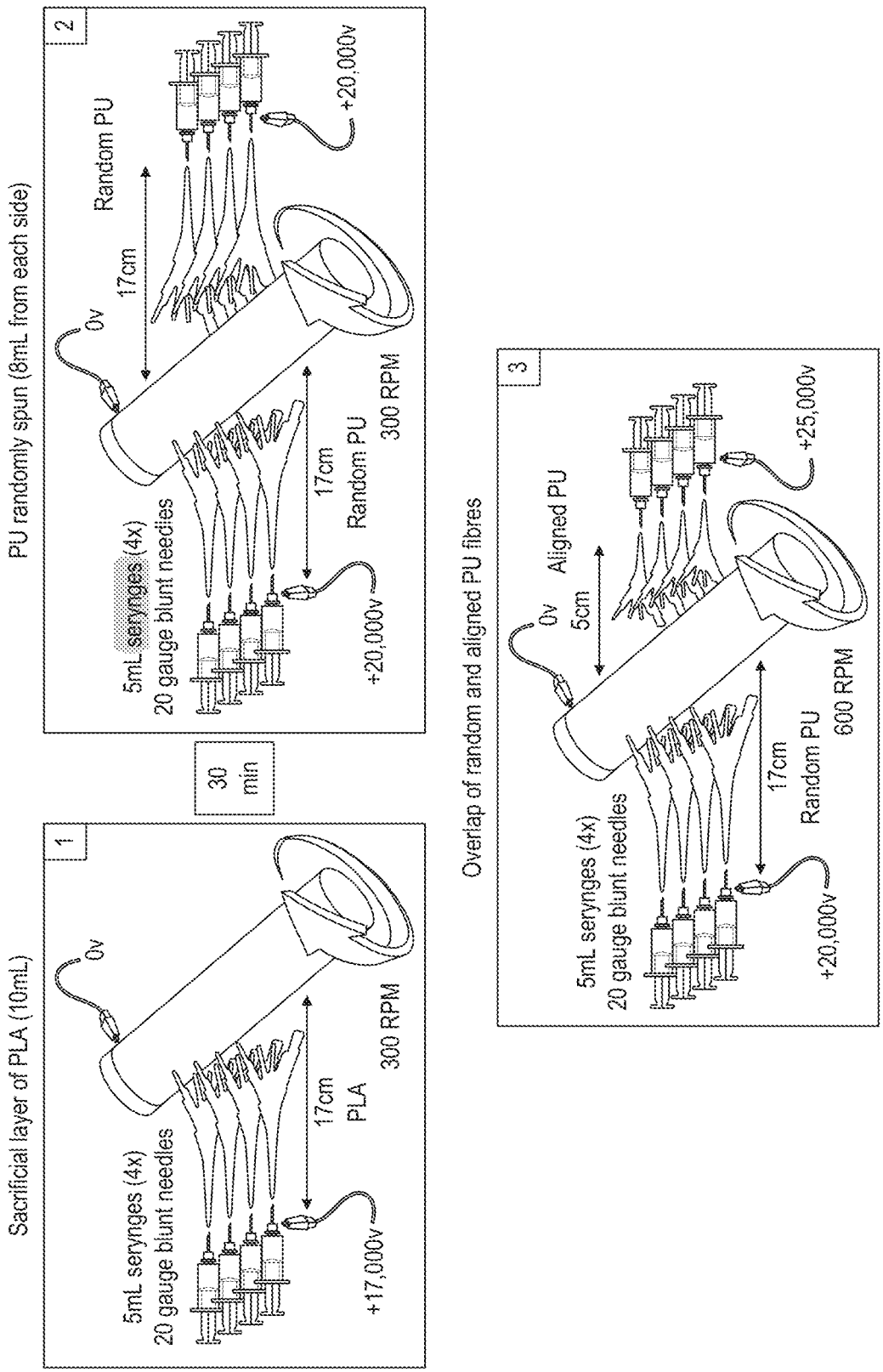
FIG. 5 shows steps 1-3 of a schematic of the preparation of a polyurethane (PU) scaffold of the present invention. In step 1, a sacrificial layer of PLA is electrospun, in step 2 a random layer of polyurethane is electrospun, in step 3 there is an overlap wherein the first layer of randomly electrospun polyurethane and a second aligned layer of polyurethane fibres are both spun simultaneously.
Figure 6:
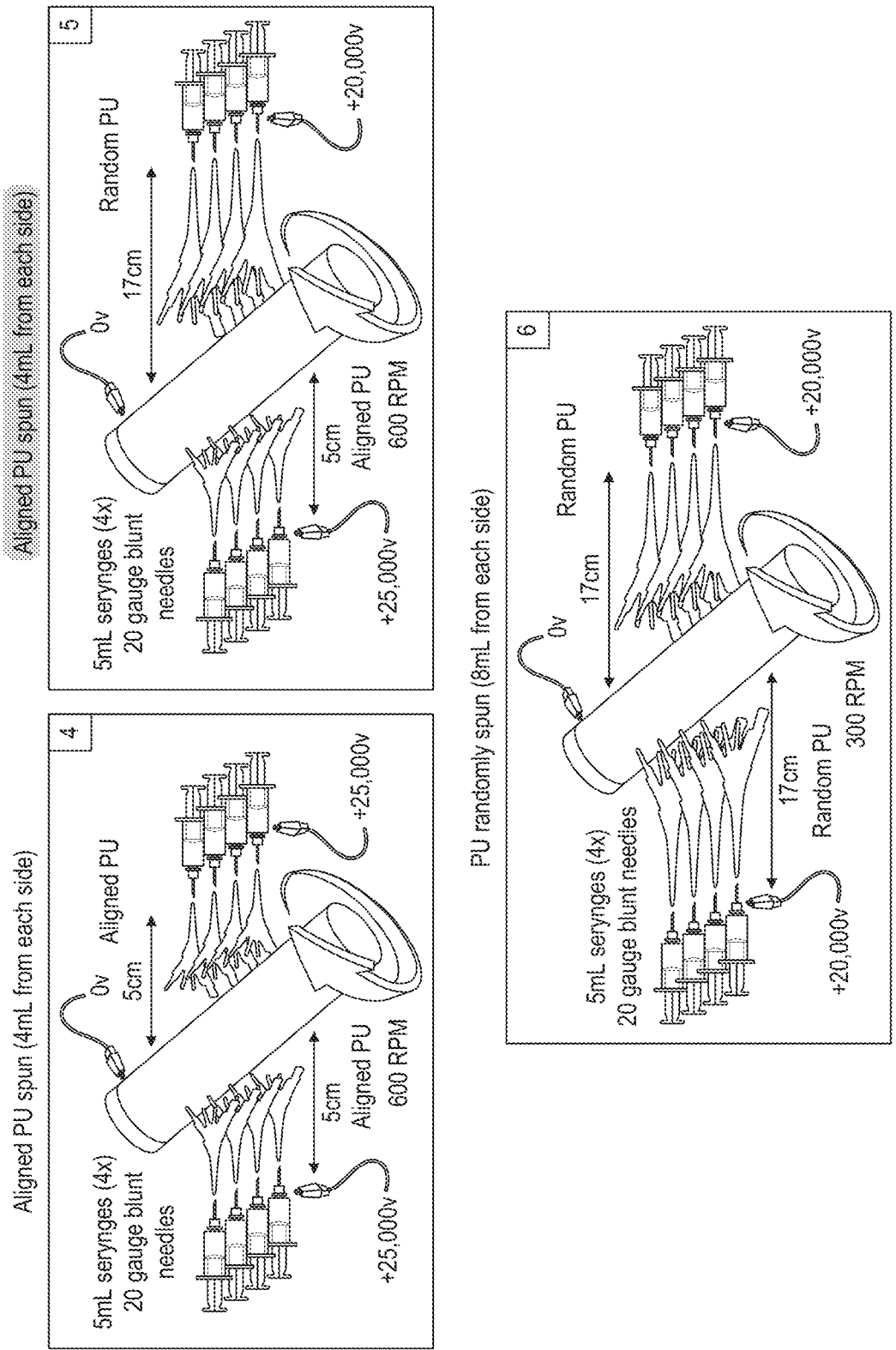
FIG. 6 shows steps 4-6 of a schematic of the preparation of a polyurethane (PU) scaffold of the present invention. In step 4, the electrospinning of the first layer of randomly electrospun polyurethane has ceased and only the second layer aligned is electrospun, in step 5 there is an overlap wherein the second layer of aligned electrospun polyurethane and a third layer of randomly electrospun polyurethane fibres are both spun simultaneously, in step 6 only the third layer of randomly electrospun polyurethane fibres is spun.

Hence, no two layers are fully intermixed. FIGS. 5 and 6 show a preferred method of the invention.

Suitably, the sacrificial layer may be applied to a surface rotating from about 200 to 400 rpm or from about 250 to 350 rpm. Suitably, the sacrificial layer may be applied to a surface rotating at about 300 rpm.

Suitably, the sacrificial layer may be produced with a needle to surface distance of from about 12 cm to 17 cm or from about 14 cm to 17 cm. Suitably, the sacrificial layer may be produced with a needle to surface distance of about 17 cm.

Suitably, the sacrificial layer may be produced by delivering polymer solutions at a rate of from about 30 µl/min to 40 µl/min per syringe with an accelerating voltage of from about 15 kV to 19 kV DC.

Suitably, step b may be conducted after any excess solvent from step a. has evaporated. For example, step b. may be conducted at least 5 minutes or at least 10 minutes or at least 15 minutes or at least 20 minutes or at least 25 minutes after step a. finishes. Suitably, step b. may be conducted about 30 minutes after step a. finishes.

Suitably, the first and/or third layers may be applied to a surface rotating from about 200 rpm to 400 rpm or from about 250 rpm to 350 rpm. Suitably, the first and/or third layers may be applied to a surface rotating at about 300 rpm.

Suitably, the first and/or third layers may be produced with a needle to surface distance of from about 17 cm to 23 cm or from about 17 cm to 20 cm. Suitably, the first and/or third layers may be produced with a needle to surface distance of about 20 cm.

Suitably, the second layer may be produced with a needle to surface distance of from about 5 cm to 10 cm or from about 5 cm to 7 cm. Suitably, the second layer may be produced with a needle to surface distance of about 5 cm.

Suitably, the first and/or third layer may be produced by delivering polymer solutions at a rate of from about 30 µl/min per syringe to 40 µl/min per syringe or from about 30 µl/min per syringe to 40 µl/min per syringe; with an accelerating voltage of from about 17 kV DC to 23 kV DC or from about 19 kV DC to 21 kV DC. Suitably, the first and/or third layer may be produced by delivering polymer solutions at a rate of from about 40 µl/min per syringe with an accelerating voltage of from about 20 kV DC.

Suitably, the second layer may be applied to a surface rotating from about 500 rpm to 700 rpm or about 550 rpm to 650 rpm. Suitably, the second layer may be applied to a surface rotating from about 600 rpm.

Suitably, the second layer may be produced by delivering polymer solutions at a rate of from about 30 µl/min per syringe to 40 µl/min per syringe or from about 30 µl/min per syringe to 40 µl/min per syringe; with a voltage of from about 21 kV DC to 25 kV DC or from about 21 kV DC to 23 kV DC. Suitably, the first and/or third layer may be produced by delivering polymer solutions at a rate of from about 40 µl/min per syringe with an accelerating voltage of from about 23 kV DC.

Suitably, the humidity during the electrospinning of the sacrificial layer may be about 30%.

Suitably, the amount of polymer used in each layer can be modified according to desired use and/or to yield a desired thickness or ratio between the layers. For example, it may be desirable for the scaffold to have a cross-section which is about 2:1:3 (first layer to second layer to third layer).

A more detailed method of producing a scaffold of the present invention follows. This method provides preferred ranges of conditions for the method.

The poly-L-lactic acid which may be used as a sacrificial layer in the method of the invention may be used in any suitable concentration. Suitably, a concentration of PLA at about 10% wt/v to about 15% wt/v may be used. Suitably, the concentration may be about 10% wt/v.

The poly-L-lactic acid may be dissolved in any appropriate solvent or combination of solvents. Suitably, the solvent may be dichloromethane (DCM).

The polyurethane used to electrospin the first, second and/or third layer may be used in any suitable concentration. Suitably, a concentration of polyurethane at about 10% wt/v to about 15% wt/v may be used. Suitably, the concentration may be about 10% wt/v.

The polyurethane may be dissolved in any appropriate solvent or combination of solvents. Suitably, one example of an applicable solvent is 60:40 to 70:30 Dimethylformamide (DMF):Tetrahydrofuran (THF). Suitably, the solvent may be 70:30 Dimethylformamide (DMF):Tetrahydrofuran (THF).

A sacrificial PLA layer of random fibres may be produced in accordance with step a., by delivering a suitable amount of the polymer solution comprising PLA towards a rotating mandrel. Suitably, about 5 ml to 10 ml may be used. Suitably, about 10 ml may be used.

The polymer solution may be divided between an appropriate number of syringes. For example, where 10 ml of polymer solutions comprising PLA is used, the solution may be divided between 2 or more or 3 or more syringes. Suitably, the solution may be equally divided between 4 syringes. The syringes may be placed into a syringe pump (such as GenieTMPlus, Kent Scientific, USA).

PLA fibres were produced by delivering polymer solutions at an appropriate rate (e.g., from 30 µl/min to 40 µl/min) per syringe with an appropriate accelerating voltage (e.g. from 15 kV to 19 kV) DC from a high voltage supply (e.g. Genvolt, UK). The electrospun material may be collected on a covered (e.g. aluminium foil covered) earthed rotating surface (e.g. mandrel) of an appropriate size for the scaffold being produced.

A rotating speed of from 200 rpm to 400 rpm) may be used. The needle to collector distance may be 12 cm to 17 cm at 21° C. and ~30% humidity. Though a person of ordinary skill in the art could readily adapt these parameters appropriately when different temperatures or humidity levels are used.

Suitably, a break between step a. and step b. may be desired to allow any excess solvent to evaporate. The polyurethane (hereinafter PU) tri-layers may then be directly electrospun onto the surface of the PLA fibres produced in step a.

PU tri-layer scaffolds may be created using a similar set up as for the sacrificial layer. For example, by delivering a suitable amount of the polymer solution comprising PU towards a rotating surface covered with PLA fibres. Suitably, about 15 ml to 20 ml of the polymer solution comprising PU may be used. Suitably, about 20 ml may be used.

The polymer solution may be divided between an appropriate number of syringes. For example, where 20 ml of polymer solutions comprising PU is used, the solution may be divided between 2 or more or 3 or more syringes. Suitably, the solution may be equally divided between 4 syringes. The syringes may be placed into a syringe pump (such as GenieTMPlus, Kent Scientific, USA).

In the method of the present invention each PU polymer solution is electrospun such that the scaffold comprises three layers in random-aligned-random orientations.

Random fibres may be produced by delivering polymer solutions at a rate from 30 µl/min to 40 µl/min per syringe with an accelerating voltage of about 17 kV to 23 kV DC from a high voltage supply onto a rotating surface rotating at from about 200 rpm to about 400 rpm.

Suitably, the needle to collector distance may be from about 12 cm to 17 cm at 21° C. and ~30% humidity. However, a person of ordinary skill in the art could readily adapt these parameters appropriately when different temperatures or humidity levels are used.

Aligned fibres may be produced using a voltage from about 21 kV to 25 kV, and a rotating surface of about 500 rpm to 700 rpm, such as 600 rpm. Suitably, the needle to collector may be from about 5 cm to 10 cm), preferably about 5 cm.

Interwoven random-aligned-random fibre morphologies may be produced using two separate syringe pumps. Suitably, each random layer may be produced using e.g. about 16 mls of polymer and e.g. about 8 ml may be used for the aligned layer, with e.g. a 4 ml overlap between separate layers. For example, this could be achieved using at least one syringe pump delivering random fibres, and at least one syringe pump delivering aligned fibres. With this set up, it is possible to obtain 40:20:40 for proportions of the polymer amount of each layer. It is a matter of routine to adjust the mounts of polymer used in each layer to obtain a different desired ratio between the layers.

Suitably, the sacrificial layer may readily be removed from the tri-layer scaffold without the need for further processing techniques.

The properties of the electrospun materials can be adjusted in accordance with the needs and specifications of the cells to be suspended and grown within them. The porosity, for instance, can be varied in accordance with the method of making the electrospun materials matrix.

There are many factors involved in the electrospinning process which may affect scaffolds fibre diameter and pore size. The key variables are solution viscosity, surface tension, and viscoelasticity of the spinning solution. These are directly related to the concentration of, and molecular weight of the polymer, as well as the solvent used. The dielectric properties of the solution also play a key role (Kowalczyk et al., 2008).

Another source of variation in electrospinning, which is perhaps not well documented, is that once the polymer is in solution it can change or degrade on storage and the same concentration of polymer does not always yield a solution with the same viscosity. Thus the molecular weight of the polymer will decrease rapidly over time (particularly the 50/50 PLGA). Therefore, fresh polymer is preferably used for spinning.

In a further aspect, the present invention relates to a scaffold produced by the method of the present invention. Suitably, the scaffold may have the properties of a scaffold as disclosed herein.

In another aspect, the present invention provides a scaffold of the present invention or produced by a method of the invention for use as a medicament.

In further aspect, the present invention provides a scaffold of the present invention or produced by a method of the invention for use in the treatment of stress urinary incontinence.

In another aspect, the present invention provides a method of preparing a scaffold for treatment of stress urinary incontinence wherein the method comprises using additive manufacturing methodologies (e.g. three-dimensional printing). Advances in three-dimensional printing has led to the printing of biocompatible materials. Such 3D bioprinting can be used to create complex 3D materials. Bioprinting of 3D materials are known to a person of ordinary skill in the art. For example, bioprinting of 3D materials have been described by using layer-by-layer methodology in which the settings can be readily adapted by a person of ordinary skill in the art to produce fibres with different orientations in each layer without restrictions of structural complexity and spatial heterogeneities. The method is thus able to mimic the natural structure of the target tissue in a precise and controlled placement (Hong et al. 2018).

As used herein, "urinary incontinence" (abbreviated UI) refers to any involuntary leakage of urine. It can be a common and distressing problem, which may have a profound impact on quality of life. Urinary incontinence usually results from an underlying treatable medical condition but is under-reported to medical practitioners.

As used herein, "stress urinary incontinence" (abbreviated SUI), also known as effort incontinence, refers to a urinary incontinence condition due essentially to insufficient strength of the pelvic floor muscles.

It is the loss of small amounts of urine associated with coughing, laughing, sneezing, exercising or other movements that increase intra-abdominal pressure and thus increase pressure on the bladder. The urethra is supported by fascia of the pelvic floor. If this support is insufficient, the urethra can move downward at times of increased abdominal pressure, allowing urine to pass. Most lab results such as urine analysis, cystometry and postvoid residual volume are normal. Some sources distinguish between urethral hypermobility and intrinsic sphincter deficiency (Haliloglu et al. 2010). The latter is rarer, and requires different surgical approaches.

As used herein, "mesenchymal stem cells" refers to multipotent stem cells that can differentiate into a variety of cell types, including: osteoblasts (bone cells), chondrocytes (cartilage cells), and adipocytes (fat cells).

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent, or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

EXAMPLES

Production of a Polyurethane Tri-Layer Using a Sacrificial Poly-L-Lactic Acid Layer, Analysis of Cell Penetration Methods Polymers
Poly-L-lactic acid (PLA) was purchased from Goodfellow (Cambridge, UK), polyurethane Z3A1 (Z3) was purchased from Biomer technologies (Cheshire, UK). PLA at 10% (wt/v) was dissolved in dichloromethane (DCM), Z3 was dissolved in 70:30 DMF:THF at 10% (wt/v).

Electrospinning Polyurethane tri-layer scaffolds were created by loading solutions of PU Z3 into 5 ml syringes fitted with blunt tipped 21 G needles, placed into a syringe pump (Genie™Plus, Kent Scientific, USA). Tri-layers consisted of random-aligned-random orientations. Random fibres were produced by delivering polymer solutions at a rate of 40 µl/min per syringe with an accelerating voltage of 20 kV DC from a high voltage supply (Genvolt, UK) and collected on an aluminium foil covered earthed mandrel (80 mm diameter, 160 mm length) rotating at 300 rpm, with a needle to collector distance of 20 cm at 21° C. and ~30% humidity. Aligned fibres were produced using a voltage of 23 kV, a mandrel rotation speed of 600 rpm and a needle to collector distance of 5 cm.

Interwoven random-aligned-random fibre morphologies were produced using two separate syringe pumps. Each layer was produced using 20 mls of polymer, using a 5 ml overlap between separate layers (one syringe pump delivering random fibres, while the other pump delivered aligned fibres).

The sacrificial PLA layer of random fibres was produced by delivering 10 mls of the polymer solution towards the rotating mandrel using the same steps for random fibre production above.

A 30 minute break period between separate polymer delivery (PLA and PU Z3) was performed to allow any excess solvent to evaporate. PU Z3 tri-layers were then directly electrospun onto the surface of the PLA fibres.

The PLA layer was readily removed from the PU Z3 tri-layer, without the need for further processing techniques. There was no gross delamination of the individual layers of the PU Z3 tri-layer. Scaffolds were allowed to dry for 12 hours at room temperature, prior to packaging in vacuum packs and were stored at −20° C.

Adipose-Derived Mesenchymal Stem Cell (ADSC) Culture
ADSC were isolated from human subcutaneous fat, donated by patients giving informed consent under a research tissue bank license (number 08/H1308/39) under the Human Tissue Authority, isolated and cultured. Cells were cultured in DMEM supplemented with 10% (v/v) fetal calf serum (FCS) (Advanced Protein Products, Brierley Hill, UK), 2 mM glutamine, 0.625 µg/mL amphotericin B, 100 IU/mL penicillin and 100 µg/mL streptomycin (Gibco Invitrogen, Paisley, UK).

Sample Preparation and Culture of Cells on Scaffolds
Scaffolds were cut to 1.5 cm×1.5 cm and sterilized in 70% ethanol for 20 minutes followed by 3 washes in PBS. 500,000 passage 6 ADSC were seeded per scaffold into the centre of steel rings (internal diameter 1 cm) placed onto each scaffold, creating a defined area for cell attachment. Rings were removed after 12 hours and samples cultured for 2 weeks at 37° C., 5% $CO_2$. DMEM was changed three times per week.

Scanning Electron Microscopy Assessment of Scaffolds
For imaging of cells on scaffolds these same fixed samples were processed and gold sputter coated (Edwards sputter coater S150B, Crawley, England). Samples were imaged using a Phillips XL-20 scanning electron microscope (Cambridge, UK). Fibre diameter and pore size of each scaffold was assessed.

Assessment of Cell Penetration
For imaging of live cells within scaffolds, a fluorescent dye was used to label the cells and second harmonic generation was used to image the scaffolds. 500,000 ADSC were seeded on each of the 5 sterilised scaffolds as previously described and incubated with media (DMEM) changed three times per week. Cell-scaffolds were cultured for 3 weeks, following which, 0.5 mls of serum free DMEM with 10 µM Celltracker™ red CMTPX (Invitrogen, Oregon USA) was added per well and incubated for one hour. Cells were imaged live, using a Zeiss LSM 510 Meta upright laser-scanning confocal microscope (Carl Zeiss Micro Imaging, Germany) using a 40×1.3 NA oil immersion objective attached to a tuneable (700-1060 nm) Chameleon Ti:sapphire multiphoton laser (Coherent, CA, USA) for second harmonic generation (SHG) signal. Red cell tracker signal was created by illuminating constructs at 543 nm with 30% transmission and detected between 565 nm and 615 nm. For SHG signal, constructs were illuminated at 840 nm and signals were detected between 415 nm and 426 nm. Images (512×512), with a pixel dwell time of 6.39 µs were captured at a range of depths by moving the focal plane down from the surface of the scaffold, where there was the greatest number of cells present and without any polymer fibres visible, at 1 µm intervals until no further cells were visible and polymer fibres dominated the field of view.

Results

Scanning Electron Microscopy Assessment of Scaffolds

Figure 2:
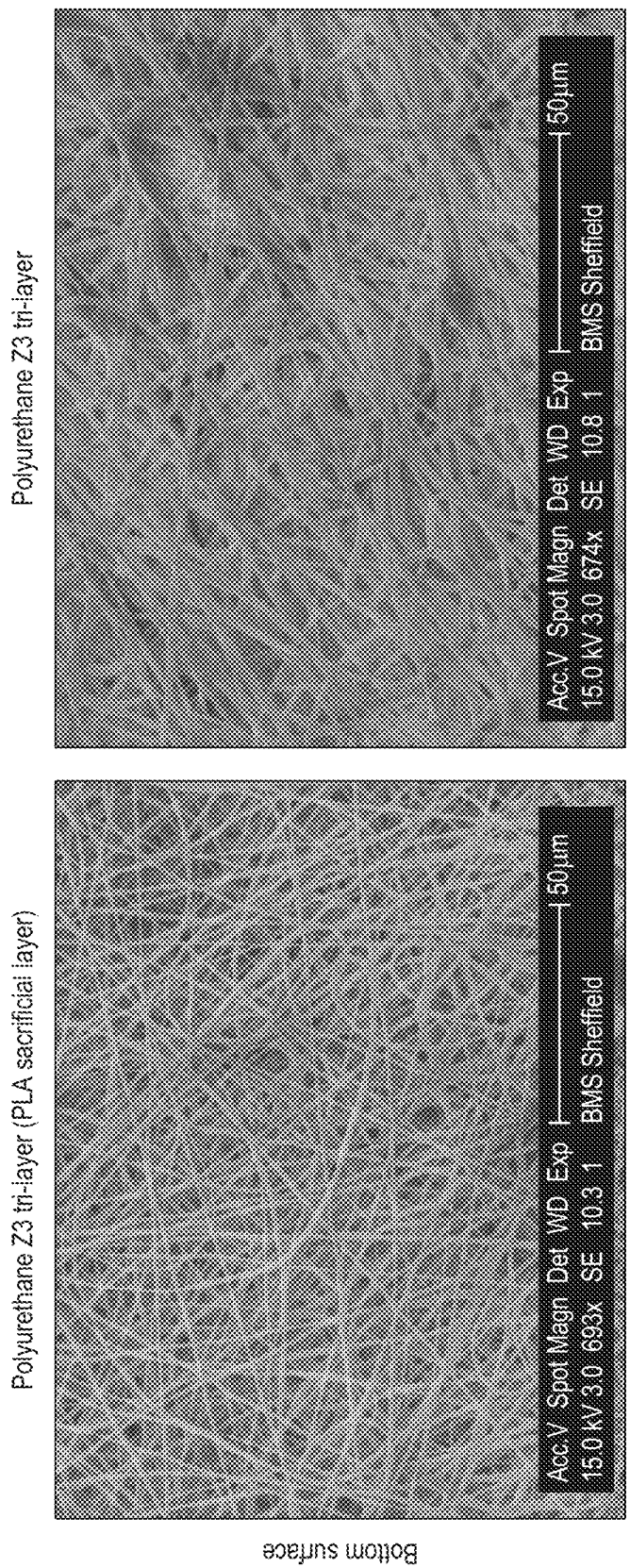
FIG. 2 shows scanning electron microscopy images of the bottom surface of the polyurethane scaffolds. The left hand picture shows the bottom surface of the polyurethane Z3 tri-layer produced using a PLA sacrificial layer. Clearly defined polymer fibres and pores between the fibres are visualised. The right hand picture shows a polyurethane tri-layer produced in a similar manner but without a PLA sacrificial layer. This shows a 'warped' polymer fibre morphology on the bottom surface of the polyurethane tri-layer scaffold without the presence of a sacrificial layer of PLA.
Figure 3:
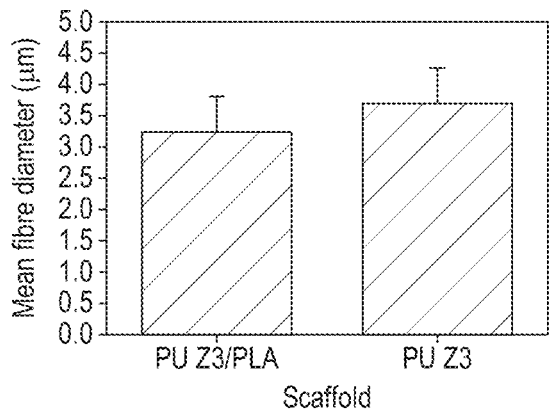
FIG. 3 shows the fibre diameter and pore size of polyurethane scaffolds. This shows that while the fibre diameter of the bottom surface of the polyurethane scaffold with a sacrificial layer is smaller than that of the plain polyurethane tri-layer, the pore size is greater for that of PU Z3/PLA.
Figure 3:
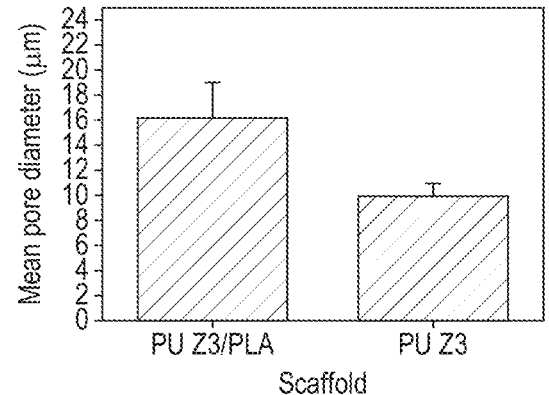
Figure 3:
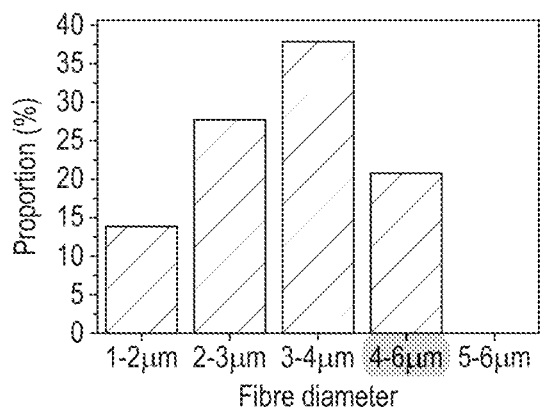
Figure 3:
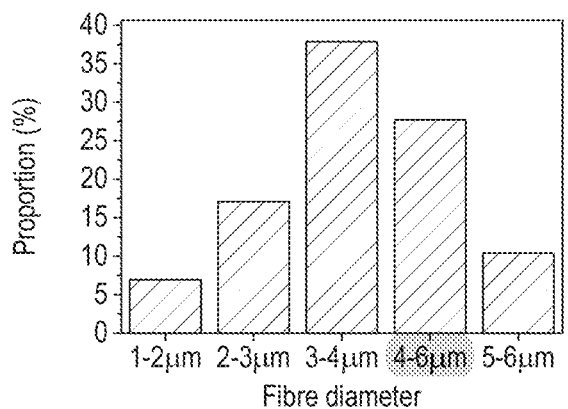
Figure 3:
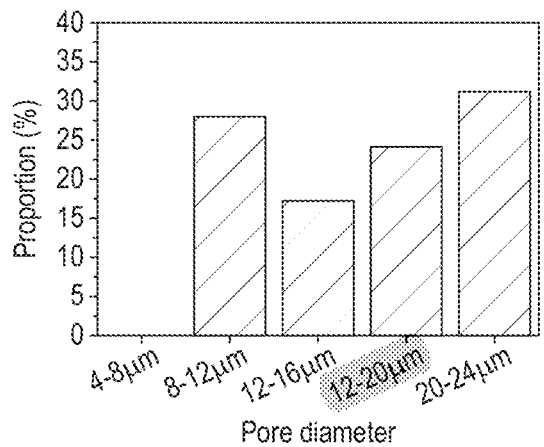
Figure 3:
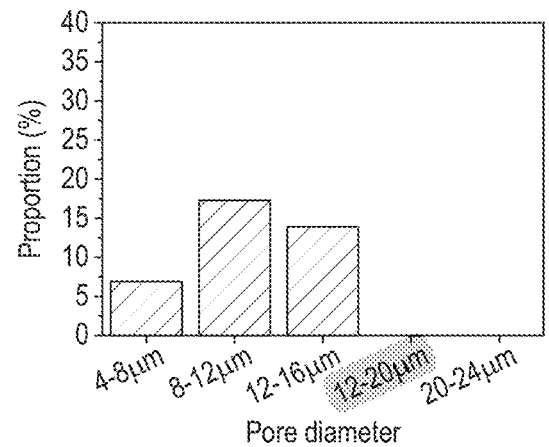

FIG. 1 and FIG. 2 demonstrates the electron microscopy images of the two produced scaffolds. The bottom surface of the tri-layer that was electrospun onto the surface of the sacrificial PLA layer demonstrates a confluent surface, while the bottom layer of the basic tri-layer shows a warped appearance. FIG. 3 demonstrate the fibre diameter and pore size of PU scaffolds. FIG. 3 demonstrates that the pore size of the bottom surface of the tri-layer that is electrospun onto the sacrificial PLA layer is much greater. This shows that while the fibre diameter of the bottom surface of the polyurethane scaffold with a sacrificial layer is smaller than that of the plain PU tri-layer, the pore size is much greater for that of PU Z3/PLA.

Assessment of Cell Penetration

Figure 4:
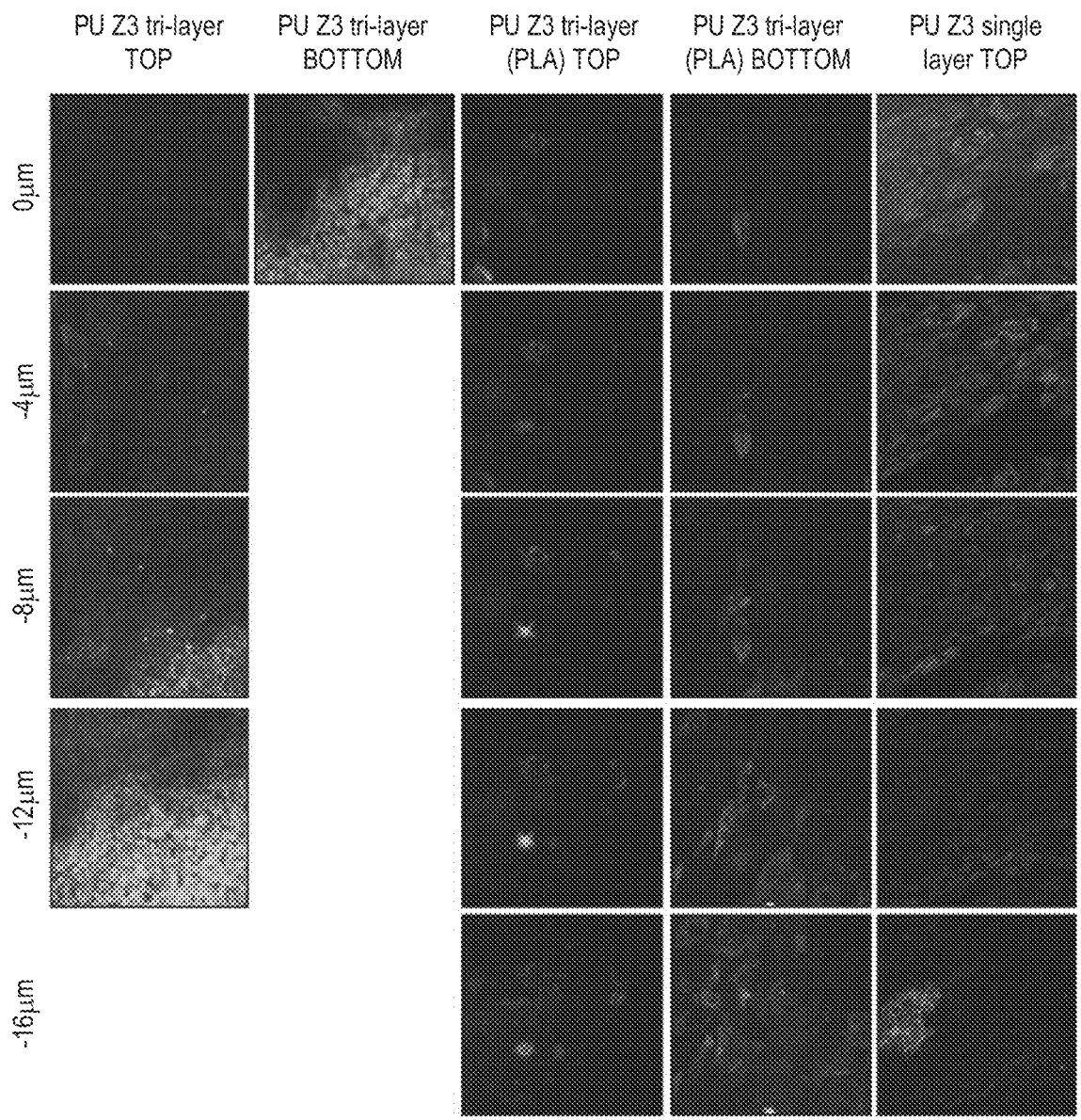
FIG. 4 shows the ability of adipose derived stem cells (in white) to penetrate between the polymer fibres at different depths from the scaffold surface. This shows that cells are better able to penetrate both the top (-TOP) and bottom (-BOTTOM) surfaces of the polyurethane scaffold with a sacrificial layer (PU Z3/PLA) than the plain polyurethane tri-layer scaffold (PU Z3). When a sacrificial layer of PLA is used both the top layer and bottom layer adipose derived stem cells penetrate to at least 16 μm whereas when adipose derived stem cells od not penetrate the bottom layer of a tri-layer prepared without the use of a sacrificial layer.

FIG. 4 shows the ability of adipose derived stem cells (in white) to penetrate between the polymer fibres at different depths from the scaffold surface, as measured using confocal microscopy. The bottom layer of the tri-layer that is electrospun onto the sacrificial PLA layer demonstrates that cells are present at greater depths than either the bottom surface of the tri-layer without the sacrificial PLA layer or the top surface of either scaffold. For the top surface of both the sacrificial and non-sacrificial tri-layer scaffolds, cells represented only a thin superficial layer, while a control that consisted of only a single random fibre orientation of Z3 fibres demonstrates a much greater cell penetrative ability. This shows cell tracker red stained cells at a variety of scaffold depths, as measured using confocal microscopy. The bottom layer of the tri-layer that is electrospun onto the sacrificial PLA layer demonstrates that cells are present at greater depths than either the bottom surface of the tri-layer without the sacrificial PLA layer or the top surface of either scaffold. For the top surface of both the sacrificial and non-sacrificial tri-layer scaffolds, cells represented only a thin superficial layer.

Conclusions

The production of a tri-layer of random-aligned-random orientated fibres represents a fascia-like structure. These scaffolds can be reliably produced using basic electrospinning equipment. However, these techniques can frequently lead to the production of a 'warped' bottom fibre surface that results from the electrospinning of polymer directly onto a flat surface.

The use of a sacrificial layer consisting of randomly orientated degradable polymer fibres that can be readily separated from the final product is a novel method for overcoming this commonly encountered problem. The use of the sacrificial layer results in improved porosity of the bottom surface of the scaffold, and the inventors demonstrate that this is associated with an improved ability of cells to penetrate the scaffold fibres and therefore this technique can potentially have an impact on the initial healing phase of a repair material following implantation.

Mechanical Testing of Scaffolds

Preparation of Scaffolds

FIGS. 5 and 6 show a schematic of the preparation of the polyurethane (PU) scaffolds. Three layers are spun—the first layer to produce random fibres, the second layer to produce aligned fibres and then the third layer to produce random fibres.

In a modification of this technique the inventors introduced an initial sacrificial layer of poly-L-lactic acid (PLA). These fibres are spun first to provide a template then the tri-layer spun onto them and then post spinning the PLA layer is gently peeled off the PU layers.

The motivation for spinning onto a random scaffold of PLA fibres was to avoid the adverse effects of residual solvent on PU fibres which tended to cause fibre merging and small voids between the fibres which would not support cell entry into the scaffolds. The PLA acts as a sacrificial template layer.

Polymers

PLA was purchased from Goodfellow (Cambridge, UK), PU Z3A1 was purchased from Biomer technologies (Cheshire, UK). PLA at 10% (wt/v) was dissolved in dichloromethane (DCM), PU was dissolved in 70:30 Dimethylformamide (DMF):Tetrahydrofuran (THF) at 10% (wt/v).

Electrospinning

A sacrificial PLA layer of random fibres was produced by delivering 10 mls of the polymer solution towards the rotating mandrel. 2 ml was loaded into each of 4 syringes (5 ml syringes) fitted with blunt tipped 21 G needles, placed into a syringe pump (GenieTMPlus, Kent Scientific, USA). PLA fibres were produced by delivering polymer solutions at a rate of 40 µl/min (from 30 µl/min to 40 µl/min) per syringe with an accelerating voltage of 17 kV (from 15 kV to 19 kV) DC from a high voltage supply (Genvolt, UK) and collected on an aluminium foil covered earthed mandrel (80 mm diameter, 160 mm length) rotating at 300 rpm, with a needle to collector distance of 17 cm at 21° C. and ~30% humidity.

A 30 minute break period between separate polymer delivery (PLA and PU) was performed to allow any excess solvent to evaporate. PU tri-layers were then directly electrospun onto the surface of the PLA fibres.

PU tri-layer scaffolds were created by loading 20 ml solution of PU into 5 ml syringes (5 ml each) fitted with blunt tipped 21 G needles, placed into a syringe pump (GenieTMPlus, Kent Scientific, USA). Tri-layers consisted of random-aligned-random orientations. Random fibres were produced by delivering polymer solutions at a rate of 40 µl/min per syringe with an accelerating voltage of 20 kV DC from a high voltage supply (Genvolt, UK) and collected on an aluminium foil covered earthed mandrel (80 mm diameter, 160 mm length) rotating at 300 rpm, with a needle to collector distance of 20 cm at 21° C. and ~30% humidity.

Aligned fibres were produced using a voltage of 23 kV, a mandrel rotation speed of 600 rpm and a needle to collector distance of 5 cm.

Interwoven random-aligned-random fibre morphologies were produced using two separate syringe pumps. Each random layer was produced using 16 mls of polymer and 8 mL for the aligned layer, using a 4 ml overlap between separate layers (one syringe pump delivering random fibres, while the other pump delivered aligned fibres). 40:20:40 proportions of the polymer amount of for each layer was obtained. However, the middle layer looks thinner (more than half than the others) because fibres are aligned occupying less space.

The sacrificial PLA layer of random fibres was produced by delivering 10 mls of the polymer solution towards the rotating mandrel using the same steps for random fibre production above.

A 30 minute break period between separate polymer delivery (PLA and PU) was performed to allow any excess solvent to evaporate. PU tri-layers were then directly electrospun onto the surface of the PLA fibres.

The PLA layer was readily removed from the PU tri-layer, without the need for further processing techniques. There was no gross delamination of the individual layers of the PU tri-layer.

Mechanical Testing of the Materials

Three materials were tested—a commercial available PP used for stress urinary incontinence (used here as a reference), a random scaffold of PU and a tri-layer scaffold of PU consisting of random, aligned and random fibres. These was produced twice by two operators—Sample 1 and Sample 2. The materials were subjected to cyclic strain up to 5 cycles applying 25% of distention.

Figure 7A:
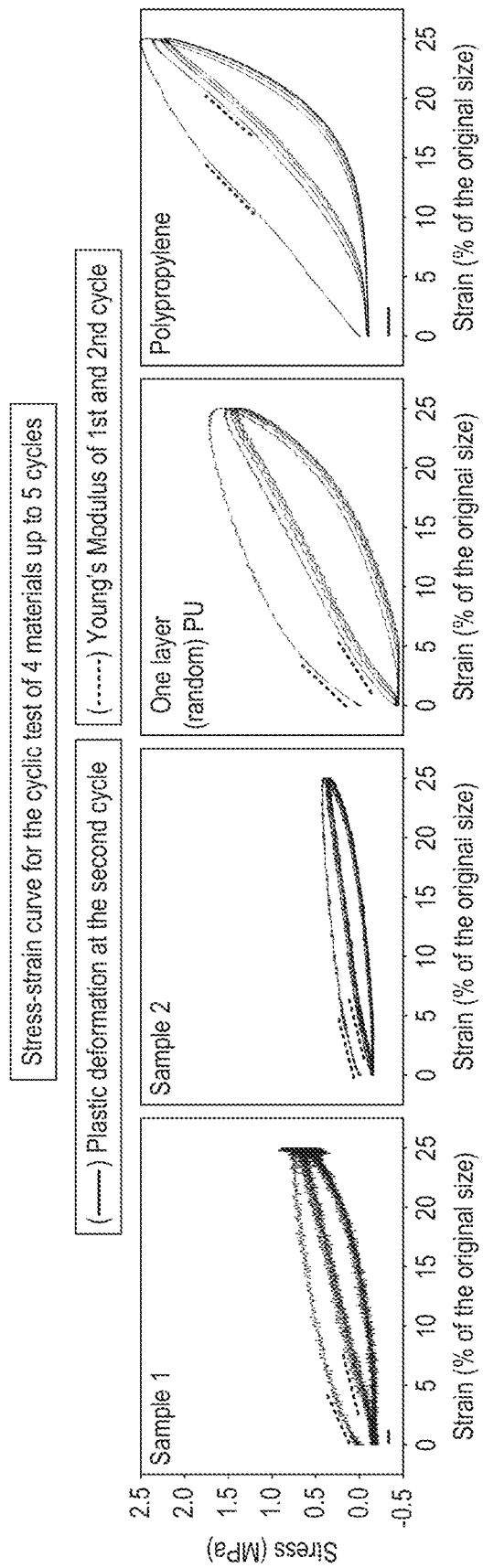
FIG. 7 shows mechanical testing data. The stress strain curves obtained are shown for these in FIG. 7A.
FIG. 7B shows the Young's modulus for the materials tested at the end of the first cycle and at the end of the second cycle.
FIG. 7C shows PU and PP samples tested for a uniaxial tensile test after 7 days cultured into an EBERS bioreactor under dynamic distention (Hillary et al. 2016). Sample 1 and sample 2 are scaffolds in accordance with the present invention, "one layer PU" refers to an electrospun scaffold of only one layer of polyurethane and "polypropylene" refers to the PP mesh which is currently used to treat SUI.
Figure 7B:
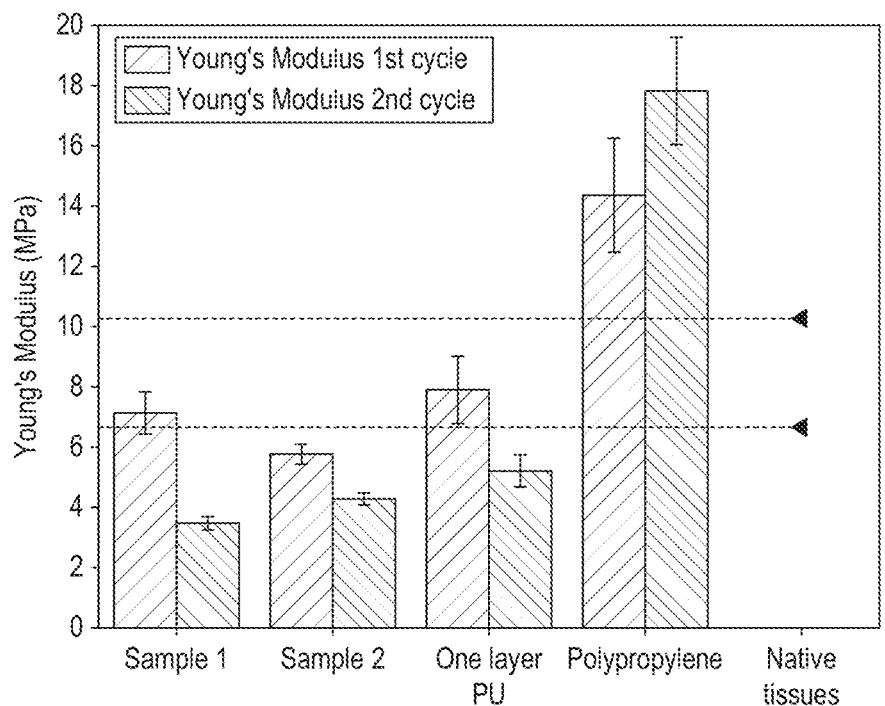

The stress strain curves obtained are shown for these in FIG. 7A. A plastic deformation at the second cycle is shown in Table 1 and the thickness of the materials in Table 2. FIG. 7B shows the Young's modulus for the materials tested at the end of the first cycle and at the end of the second cycle.

TABLE 1

Plastic deformation (%) at the second cycle

| Sample | Plastic deformation (%) at the second cycle |
| --- | --- |
| Sample 1 | 0.47 ± 0.22 |
| Sample 2 | 0.24 ± 0.14 |
| One layer pU | 0 |
| PP | 1.14 ± 0.54 |

TABLE 2

Thickness of the material (mm) measured with a digital micrometre

| Sample | Thickness of the material (mm) measured with a digital micrometre |
| --- | --- |
| Sample 1 | 0.5 |
| Sample 2 | 0.3 |
| One layer pU | 0.4 |
| PP | 0.5 |

The dotted lines in FIG. 7B show the Young's modulus reported for human healthy paravaginal tissues from Lei et al., (Lei et al., 2007). All materials showed a reduction (softening) following cyclic strain. The three PU materials have a Young's modulus that is around the lower end of the normal range, reducing slightly further after cyclical strain. In contrast the PP starts off much stiffer than the native tissues and it gets even stiffer after cyclic strain applied.

Figure 7C:
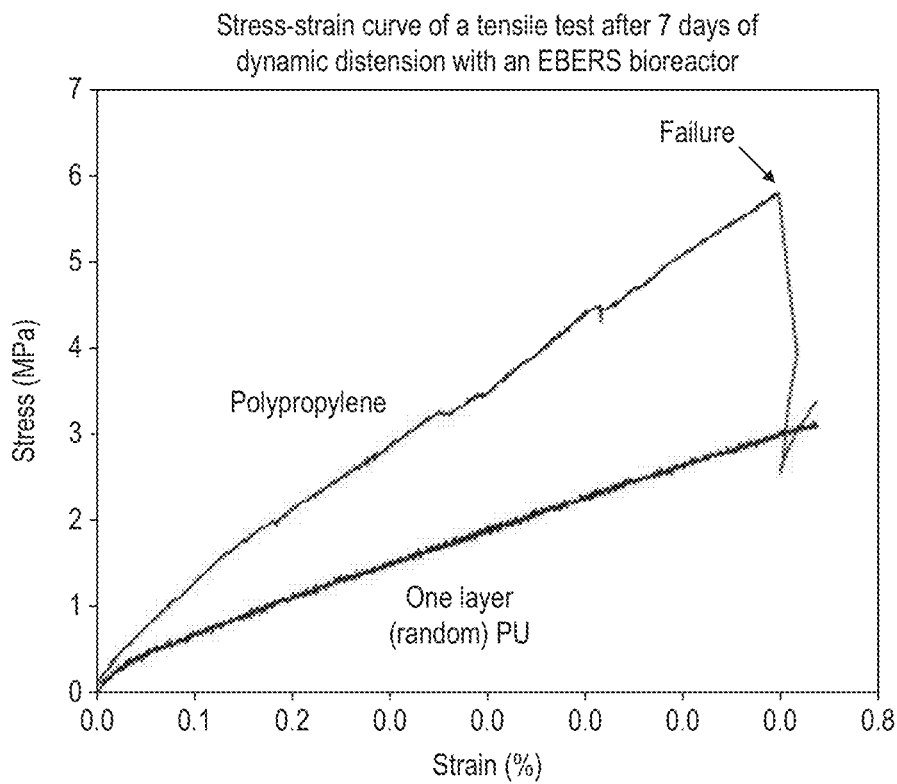

FIG. 7C shows PU and PP samples tested for a uniaxial tensile test after 7 days cultured into an EBERS bioreactor under dynamic distention (Hillary et al., 2016). While PU, in this case, one layer (random) scaffolds maintained its stretchability, PP mechanically failed by snapping during the test.

Figure 8A:
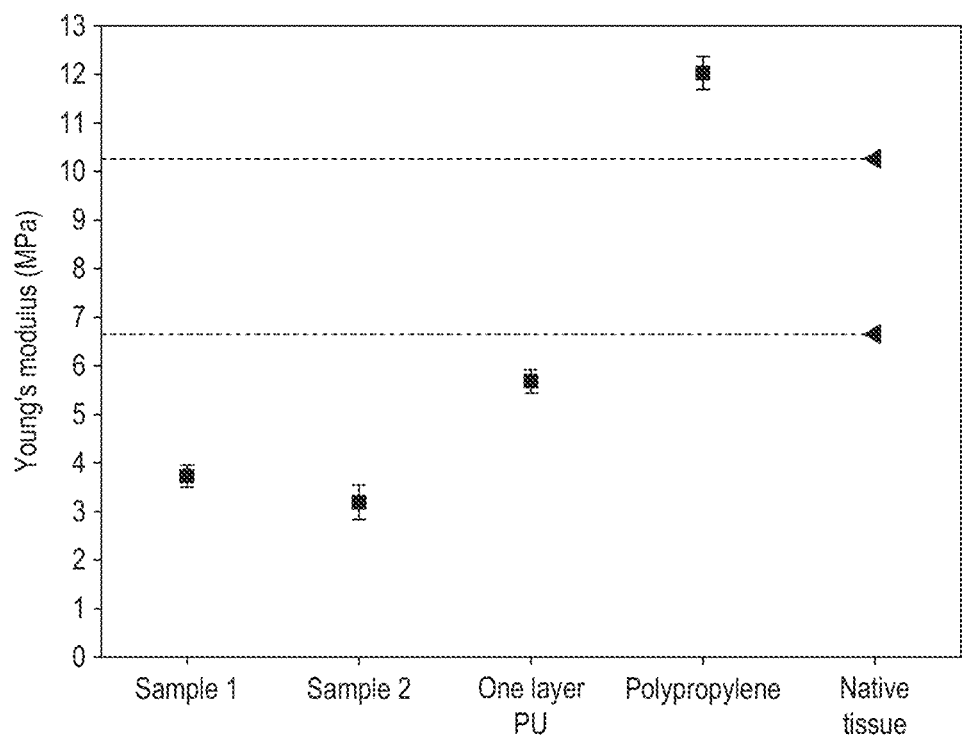
FIG. 8 summarises the values obtained for Young's modulus (A), ultimate tensile strength (B) and strain at ultimate tensile strength (C) for all of the materials following a tensile lab test.
Figure 8B:
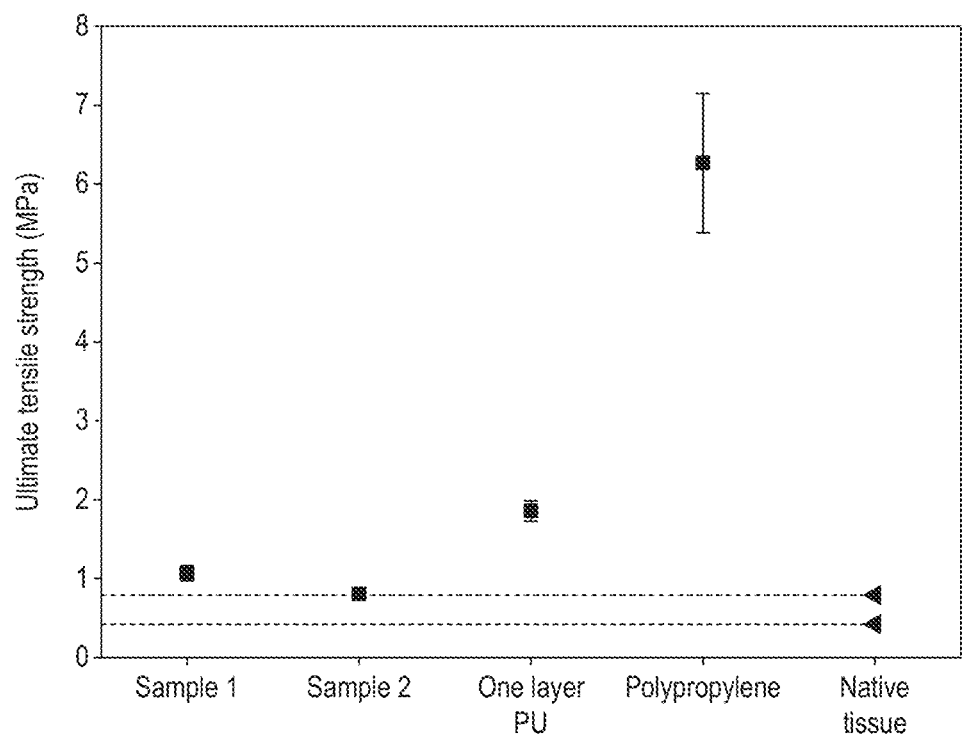
Figure 8C:
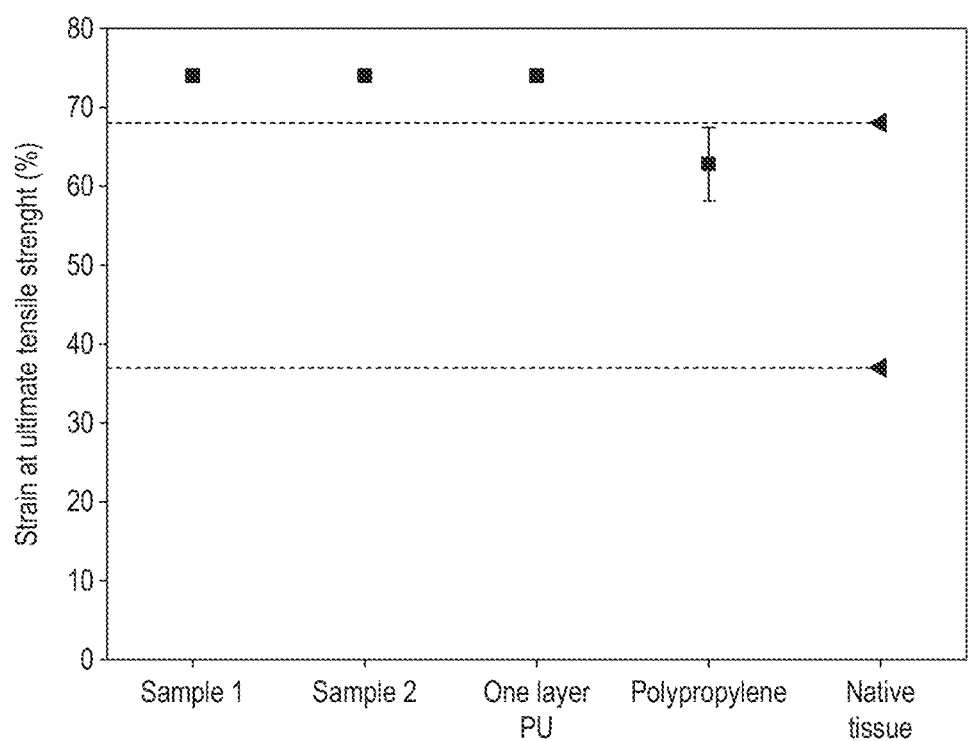

FIG. 8 summarises the values obtained for Young's modulus (FIG. 8A), ultimate tensile strength (FIG. 8B) and strain at ultimate tensile strength (FIG. 8C) for all of the materials following a tensile lab test. Again the dotted lines indicate the reference values for normal patient's tissues. This shows that with respect to Young's modulus, PP is much stiffer while the PU materials are softer than the native tissues. With respect to ultimate tensile strength PP is much stronger than the native tissues. PU materials are slightly stronger than the native tissues. Finally the strain at ultimate tensile strength, the PU materials can extend slightly more than the native tissues, the PP material is within the range of normal tissue. PP is a very stiff and strong material for the pelvic floor environment as compared to human native tissues from that area. One layer random PU seems to be slightly stiffer and stronger than the tri-layer scaffolds.

Mechanical Testing of the Scaffold Materials Before and After Dynamic Conditions Strips of all scaffolds materials, including PP as a reference material, were measured, cut and clamped to a tensiometer (BOSE Electroforce test instruments, Minnesota, USA) with a 22 N load cell. Mechanical properties were measured using a ramp test at a rate of 0.1 mm/s or a cyclic test at rate of 1 mm/s up to 25% of displacement (from its original length) at 5 cycles.

Strips from all materials measuring 3 cm×1 cm were cut and clamped in an EBERS bioreactor. Chambers were filled with DMEM and all samples were under cyclic uniaxial distension was set at 25% elongation, 0.1 mm/s rate and 18 cycles per minute over 7 days at 37° C., 5% $CO_2$. Thereafter, samples were tested for both ramp and cyclic tensile uniaxial tests as described above.

Stress vs strain plots were shown as strength (y axis, MPa) by % of displacement (x axis, %) for example in FIG. 7C. The linear gradient of each plot was taken as the Young's modulus (MPa) which is used to measure stiffness of the material. Values for Young's modulus and ultimate tensile strength are represented as compared to values derived for healthy paravaginal tissues (Lei at al. 2007), for example in FIG. 8.

The Appearance of the Tri-Layer Materials

Figure 9A:
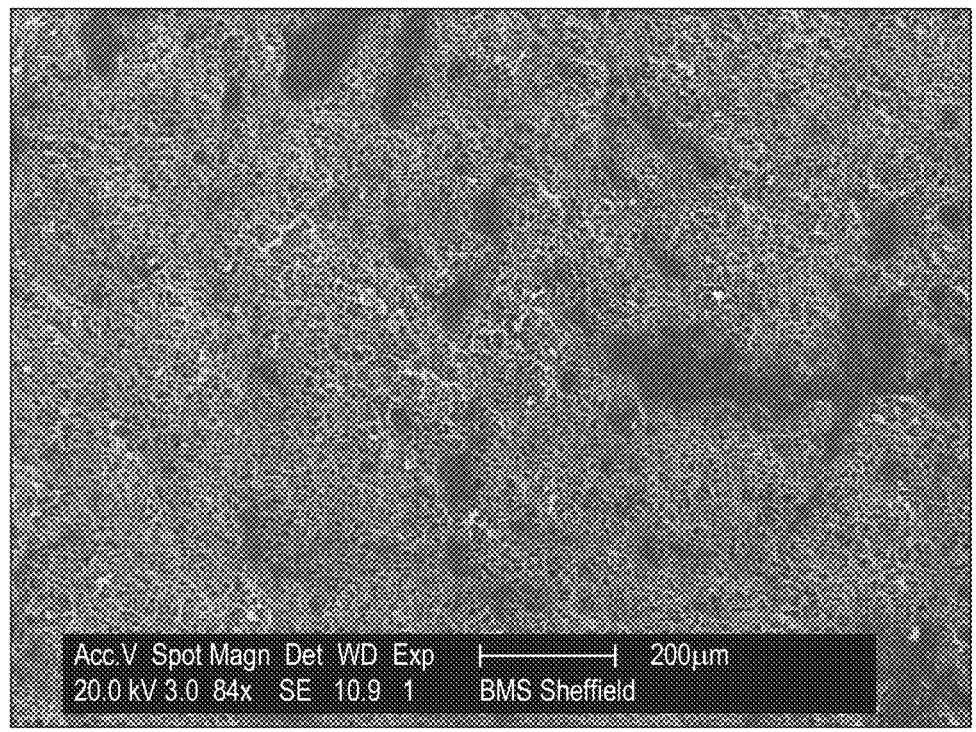
FIG. 9 shows, using scanning electron microscopy (SEM), random PU fibres which have been spun directly onto the collector using the same solution described for the tri-layers. The bottom (A) surface shows some merging of the fibres almost certainly due to solvent evaporation. The upper surface (B) shows an open porous network.
Figure 9B:
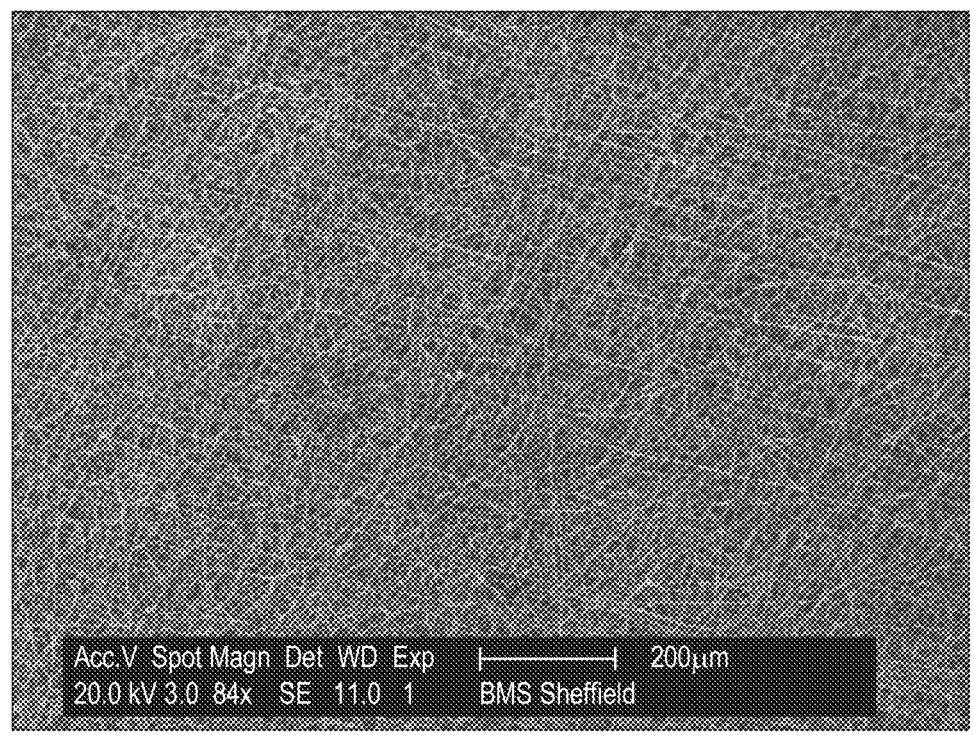
Figure 10A:
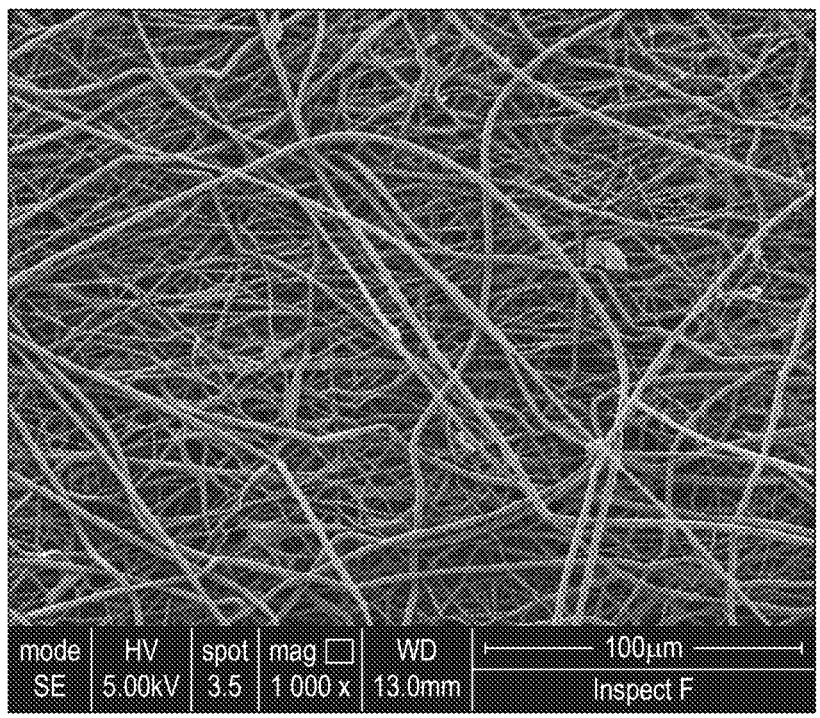
FIG. 10A shows the first layer which has been deliberately spun onto PLA fibres. This shows some residual fibres of PLA which are much thicker, around 2 μm, as can be seen from FIG. 10B, whereas the PU fibres are around 1 μm diameter. Also shown is the third layer at low (FIG. 10C) and high (FIG. 10D) magnification. This shows an open network of fibres.
Figure 10B:
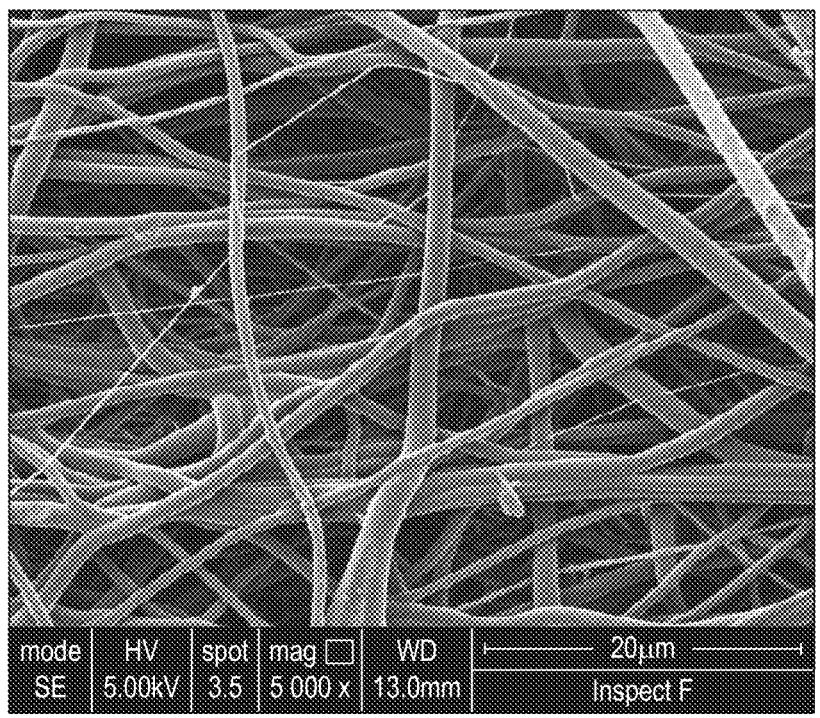
FIG. 10 shows sample 1.
FIG. 10E shows a cross section of the scaffold and has been labelled to show the areas that represent the random, the aligned and then the random fibres of this tri-layer from the SEM. The thicknesses of the three layers were calculated to be 80 μm, 30 μm and 80 μm respectively.
Figure 10C:
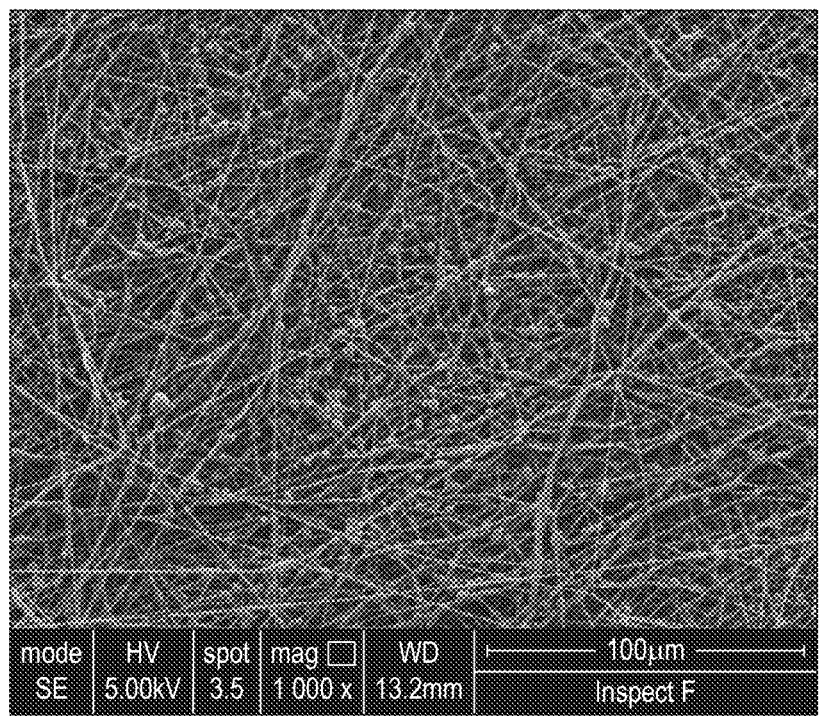
Figure 10D:
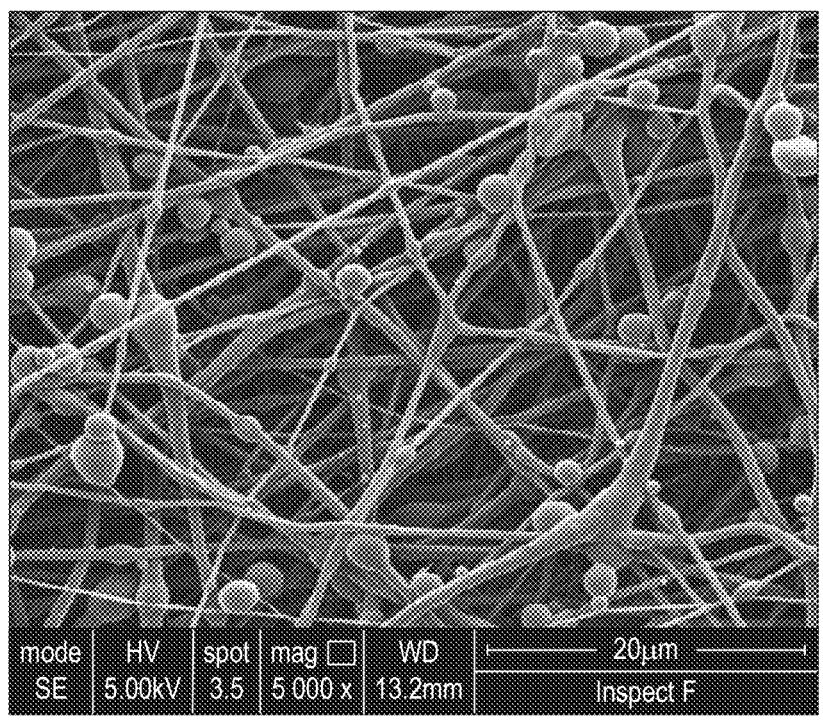
Figure 10E:
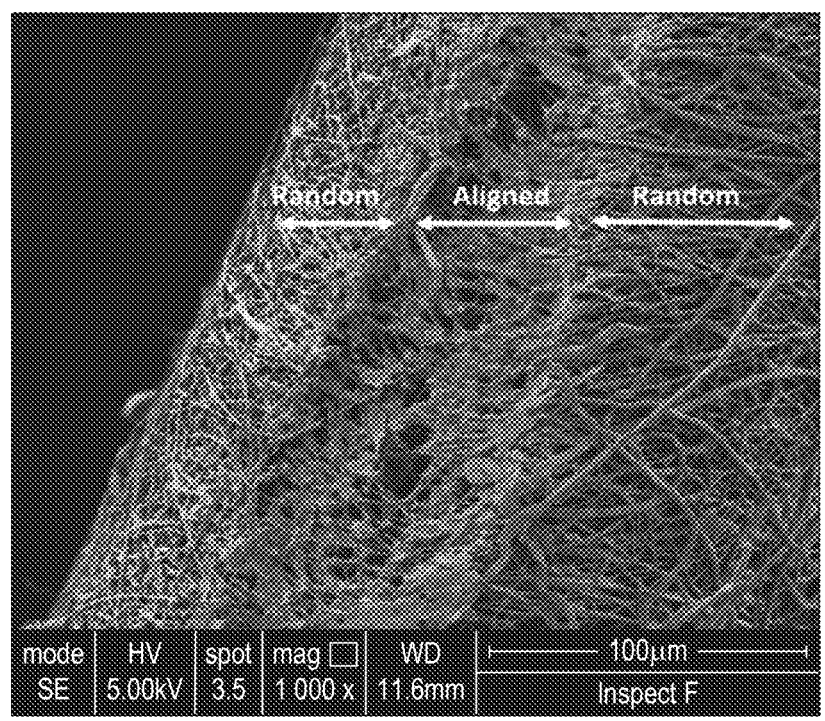
Figure 11A:
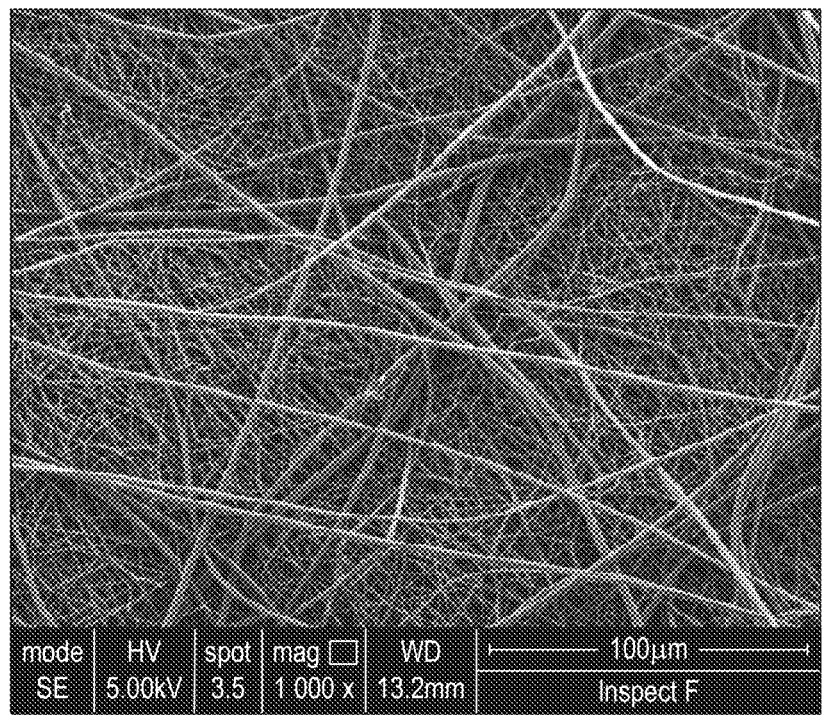
FIG. 11A shows the first layer which has been deliberately spun onto PLA. This shows some residual fibres of PLA which are much thicker around 2 μm as can be seen from FIG. 11B, whereas the PU fibres are around 0.5 μm diameter. Also shown is the third layer at low (FIG. 11C) and high (FIG. 11D) magnification. This shows an open network of fibres.
Figure 11B:
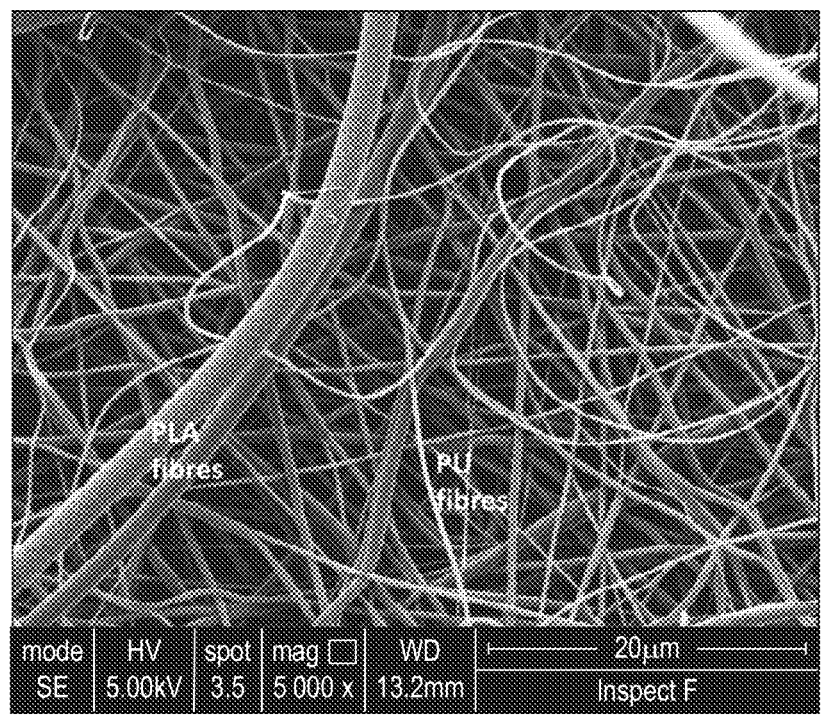
FIG. 11 shows Sample 2.
FIG. 11E shows a cross section of the material and has been labelled to show the areas that represent the random, the aligned and then the random fibres of this tri-layer from the SEM. The thicknesses of the three layers were calculated to be 50 μm, 20 μm and 50 μm respectively.
Figure 11C:
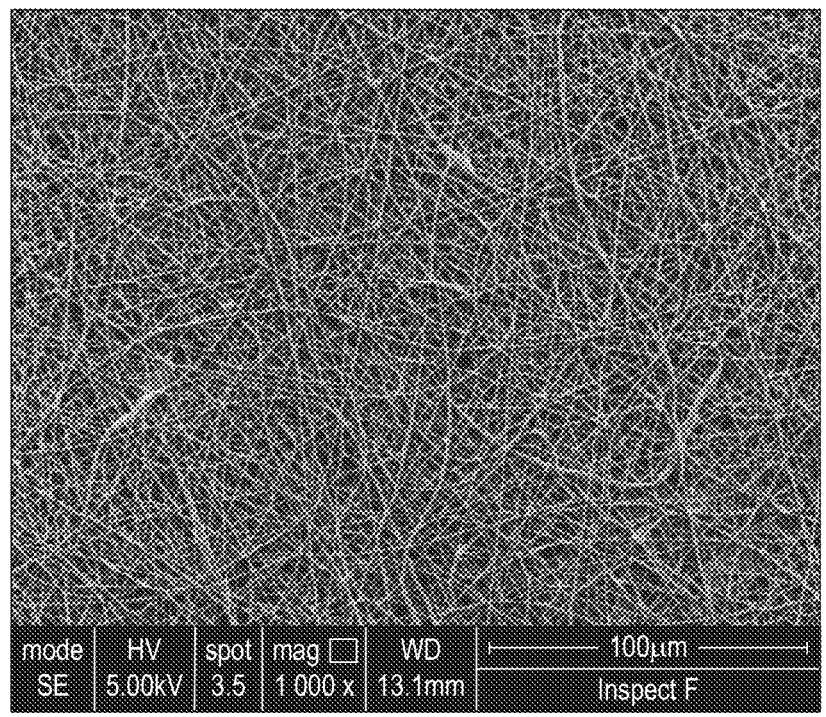
Figure 11D:
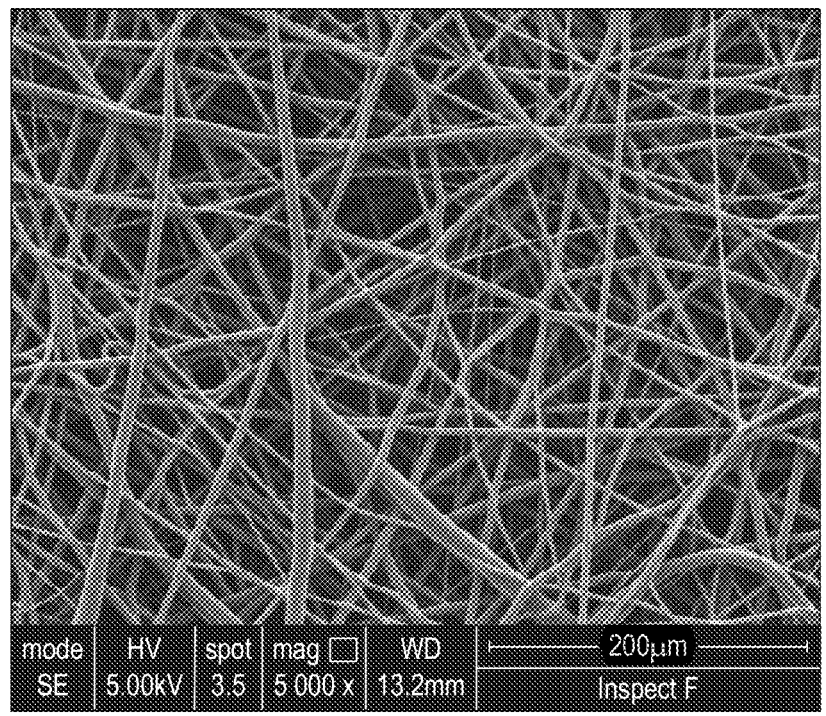
Figure 11E:
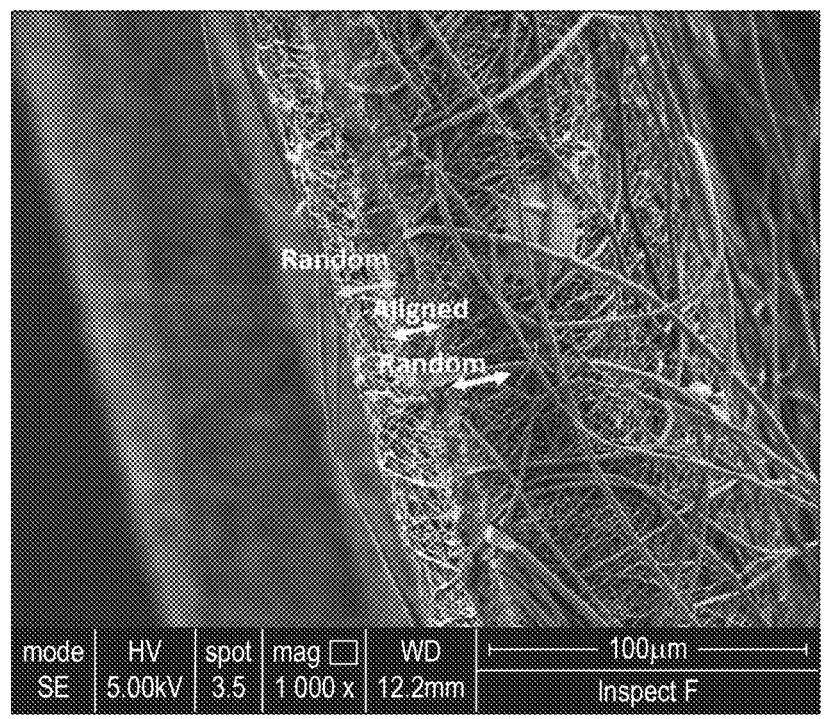

FIG. 9 shows, using scanning electron microscopy (SEM), random PU fibres which have been spun directly onto the collector using the same solution described for the tri-layers. The bottom surface shows some merging of the fibres almost certainly due to solvent evaporation. The upper surface shows an open porous network. Due to problems with solvent evaporation fibres of the bottom layer (the one in contact with foil on the collector) melt together giving very small pores. This makes it difficult for cell entry. This may explain the highest mechanical properties of this material compared with the tri-layers. A sacrificial layer of PLA when producing the tri-layer avoids this problem.

FIG. 10 (sample 1) and FIG. 11 (sample 2) show tri-layer material made on two occasions. FIG. 10 shows sample 1. FIG. 10A shows the lower surface which has been deliberately spun onto PLA fibres. This shows some residual fibres of PLA which are much thicker, around 2 μm, as can be seen from FIG. 10B, whereas the PU fibres are around 1 μm diameter. FIG. 10 shows the upper surface at low (FIG. 10C) and high (FIG. 10D) magnification. This shows an open network of fibres. FIG. 10E shows a cross section of the material and has been labelled to show the areas that represent the random, the aligned and then the random fibres of this tri-layer from the SEM. The thicknesses of the three layers were calculated to be 80, 30 and 80 respectively.

FIG. 11 shows sample 2. FIG. 11A shows the lower surface which has been deliberately spun onto PLA. This shows some residual fibres of PLA which are much thicker around 2 μm as can be seen from FIG. 11B, whereas the PU fibres are around 0.5 μm diameter. FIG. 11 shows the upper surface at low (FIG. 11C) and high (FIG. 11D) magnification. This shows an open network of fibres. FIG. 11E shows a cross section of the material and has been labelled to show the areas that represent the random, the aligned and then the random fibres of this tri-layer from the SEM. The thicknesses of the three layers were calculated to be 50 μm, 20 μm and 50 μm respectively. This values does not correspond with the values measured with the digital micrometre for analysing the mechanical testing data. The sample is cut bending its edges and placed with an angle for the SEM what makes a non-accurate measurement.

Scanning Electron Microscopy Assessment of Scaffolds

For imaging of scaffolds these same fixed samples were processed and gold sputter coated (Edwards sputter coater S150B, Crawley, England). Samples were imaged using a Phillips XL-20 scanning electron microscope (Cambridge, UK). Fibre diameter and pore size of each scaffold was assessed.

Sheep Vaginal and Abdominal Wall Biomechanical Properties after Implantation of Electrospun Meshes Methodology The study was for preclinical evaluation (biomechanics, histomorphology, local complications) of newly produced electrospun meshes (PU).

Implants were prepared in two sizes:

| | |
|---|---|
| 50 × 50 mm | abdominal implant |
| 35 × 35 mm | vaginal implant |

Groups and time points (Table 3):

TABLE 3

| Groups and time points | | |
|---|---|---|
| Time points ( days) | 60 | 180 |
| PU | 6 | 6 |

Surgical Procedure

All animals underwent simultaneous vaginal and abdominal wall implantation with single type of the implant under sterile conditions under general anaesthesia.

Experimental Surgery—Abdominal Implantation

Figures 12A, 12B:
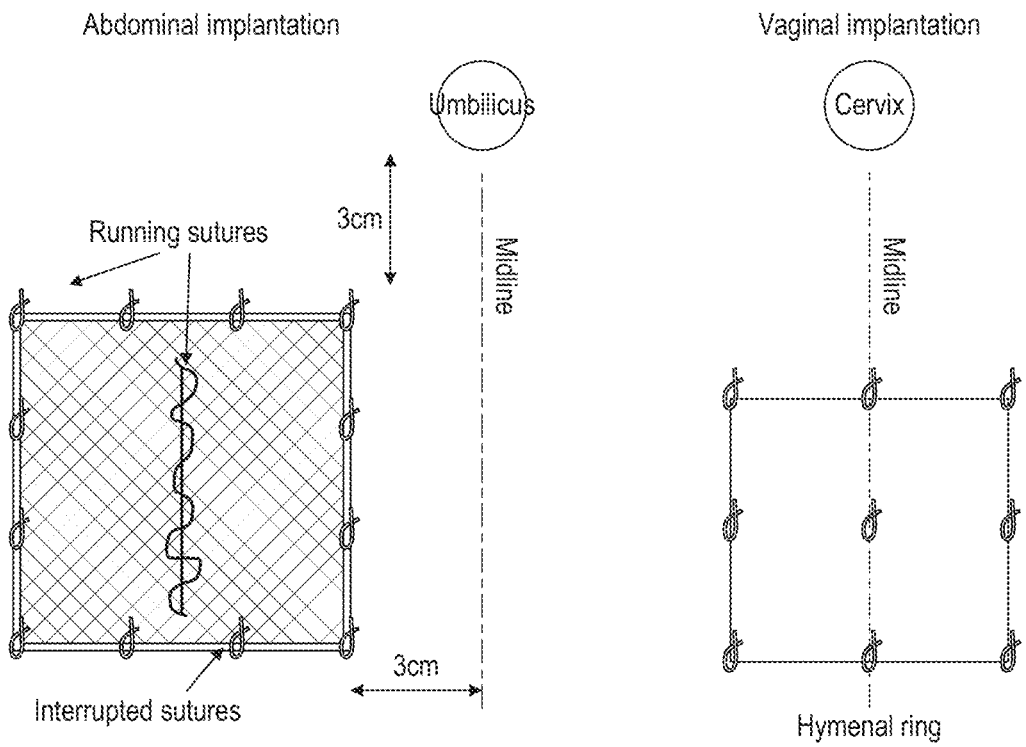
FIG. 12 shows the mesh implantation and fixation in sheep vaginal and abdominal walls.

Following anaesthesia, sheep were placed in a back lithotomy position. Lower abdominal wall was shaved and disinfected. Longitudinal 5 cm long paramedian skin incisions were made 3 cm lateral to the midline and 3 cm caudally to the umbilicus. Following lateral dissection, a 40×5 mm full thickness defect (abdominal fascia, muscles and peritoneum) were made through the abdominal wall parallel to the midline. Incision was primarily repaired with continuous running I/O polydioxanone suture (PDS II 1) and overlaid by the 50×50 mm implant. Implant was fixed tension-free with interrupted 3/0 PP sutures in the corners and with additional sutures along the borders (in the middle of the side and half of this distance) (FIG. 12A). The subcutis and skin was closed with a running 2/0 poliglecaprone (Monocryl) suture.

Experimental Surgery—Vaginal Implantation

The vagina was disinfected with polyvidinone iodide and covered by sterile wrapping. Aquadisection was performed in the posterior vaginal wall 2 cm cranially to the hymeneal ring, thereafter a longitudinal 3 cm incision was made. The rectovaginal septum was dissected by blunt and sharp dissection to create a suitable space (implant 35×35 mm) between the vaginal epithelium and rectal serosa. Implants were fixed with interrupted 3/0 prolypropylene sutures (Prolene®, Ethicon, Zaventem, Belgium) firstly in the corners and then halfway on its borders. Dry mesh will be measured with micrometre before implantation.

Postoperative Care and Analgesia

Postoperative analgesia consisted of Meloxicam (0.5 mg/kg) and Buprenorphine 0.3 mg/mL and Chlorocresol 1.35 mg/mL (Vetergesic, Ecuphar, Belgium) 1 mL/day i.m. injection up to the third day after surgery.

Animals were clinically observed for one week. Surgical sites were regularly observed to noted early postoperative complications. Sheep were euthanized at 60 or 180 days.

Mesh Explantation

Euthanasia

Sheep were euthanized at 60 and 180 days by i.v. pentobarbital (Release, Belgium) IV after sedation with Xylazine HCl (Xyl-M®; VMD; Arendonk; Belgium) 1 mL/50 kg IM injection.

Abdominal Wall Explantation

Figure 13:
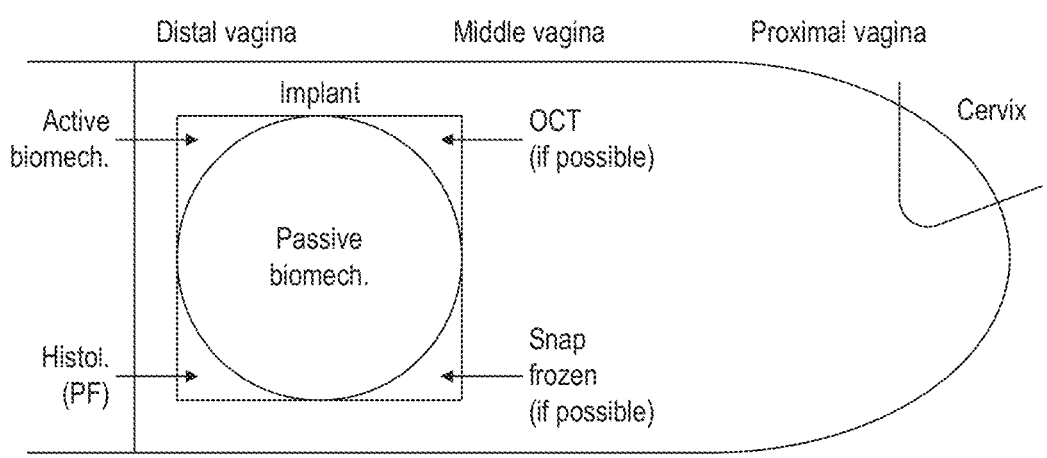
FIG. 13 shows the general view of a sheep vaginal sample containing mesh.

Abdominal explants were retrieved "en-block" following skin removal. Before obtaining the specimen picture with a ruler on side were taken. The implant with surrounding and underlying tissue and muscles (further referred as to the abdominal explant) was resected as showed in FIG. 13.

Vaginal Wall Explantation

To retrieve the vaginal implants, the vagina, urethra and the rectum were removed "en bloc" and then opened longitudinally along the urethra. The implant with ingrowth and surrounding tissue (further referred as to the vaginal explant) was further dissected to obtain these specimens (according to priority):

1. Ball burst test specimens—circular specimen (diameter 30 mm)
2. Histology—rectangular specimen—rectangular specimen (5×10 mm)
3. Contractility—1× rectangular specimen—caudal and cranial (5×10 mm)
4. OCT—rectangular specimen (5×10 mm)
5. Snap frozen Macroscopical Evaluation During dissection evaluation of the presence of herniation, erosions, fluid collections or infections was undertaken and pictures will be taken. The presence and severity of adhesion formation was documented (also by a picture). This involves documentation of the area (%) of the implant surface that was covered by adhesions. The density of adhesions was graded on a scale of 0-III, where 0 represents no adhesions, I adhesions that can be easily separated, II mild adhesions that are more difficult to separate and III dense adhesions, which can only be surgically separated (Toosie et al., 2000).

The longitudinal and transversal dimensions were measured similarly along/perpendicular to cranio-caudal body axis (analogue calliper). The later were used to calculate area reduction of the implant.

The surface of the implant was measured before implantation and at sacrifice (width and length at 3 levels). Proportional shrinkage will be defined as % shrink=(surface of the implant at implantation minus surface of the implant at sacrifice)/surface at implantation×100%.

Assessment of the Explant
Tissue Collection and Histological Analyses
1. 1.0×0.5 cm tissue pieces fixed in 10% neutral buffered formalin overnight, washed in PBS for 2 hours and stored in Ethanol 70% before embedding
2. Specimens were embedded in paraffin and cut into 6 μm slices in a longitudinal fashion so that each slice contained the implant, interface and surrounding native tissue. 3. Sections were stained with
  a. Haematoxylin & Eosin—basic inflammatory reaction (FBGC, PMN according to Badylax)
  b. Trichrome—morphometry
  c. Alpha-smooth muscle actin (α-SMA)—smooth muscle content (1:200 dilution)
  d. CD34 vascularisation (1:2000 dilution)
  e. CD 45—lymphocytes (1:200 dilution)
  f. HLA-DR, CD163 Macrophages subtypes (M1 and M2 respectively) (1:100 and 1:300 dilution, respectively)
  g. PGP9.5 Innervation staining (1:1000 dilution)

Histologic Assessment
H&E Stains

Sections for H&E staining were deparaffinized with xylene for 2 min and then re-hydrated in 2 changes in IMS from 100% absolute alcohol (1 min) to 70% alcohol (30 sec). After this, samples were washed for 1 min in distilled water, and were stained in Harris haematoxylin for 1 min and 30 sec. After another wash in running tap water for 4 min samples were stained in eosin for 5 min. Then, samples were dehydrated in 70% alcohol (IMS) by dunking the samples and then in 100% alcohol for 30 sec. Finally, they were cleaned in xylene and mount with a coverslip using a DPX mounting medium.

H&E stains were performed to quantify the presence of foreign body giant cells (FBGC), polymorphonuclear (PMN) and vessels (vascularity). Five randomly chosen non-overlapping fields per slide scored at a magnification of ×400 and averaged. Fields randomly selected at the interface between the implant and surrounding tissue. An ordinal scale was used similar to that described by Badylak, where scores are made as follows: none of the cells/vessels per high-power field (score 0), 1-5 (score 1), 6-10 (score 2) and >10 (score 3).

Trichrome Stains

Sections for trichrome staining were deparaffinized and re-hydrated as above for the H&E method. Once washed in distilled water sections are incubated in Weigert's haematoxylin for 5 min and washed in running tap water for another 5 min. Then samples were washed with 1% acetic acid for 30 sec and incubated with Azophloxine solution (Reagent 1, Masson-Goldner staining kit) for 10 min. After another wash with 1% acetic acid for 30 sec samples were incubated with Tungstophosphoric acid orange G solution (Reagent 2, Masson-Goldner staining kit) for 1 min. After another wash with 1% acetic acid for 30 sec samples were incubated with Light green SF solution (Reagent 3, Masson-Goldner staining kit) for 2 min. After a final washed with 1% acetic acid for 30 sec samples were dehydrated by increased alcohol incubations from 70% IMS for 30 sec, to 96% IMS form 30 sec, to 3 washes with 100% IMS of 30 sec, 30 sec and 2 min respectively. Finally samples were washed with xylene doing 2 incubations of 2 min each. Samples were then mount with a coverslip using a DPX mounting medium.

Trichrome stains extracellular connective tissue (mainly unspecified collagen) blue. Five non-overlapping images 400× magnification were obtained and semi-quantitatively evaluated using a blind scoring done by 3 researchers for percentage of area occupied by collagen at interface mesh-surrounding tissue.

Immunohistochemistry

Sections for immunohistochemistry (IHC) were deparaffinized by 2 changes of xylene, 2 min each, and then, re-hydrated with 2 changes in 100% absolute alcohol (IMS), 2 min each, and 10 min in 95% alcohol. After this, samples were washed briefly in distilled water, and 2 washes more with Tween 20-PBS were performed of 2 min each. Sections were incubated for 10 min with hydrogen peroxide (Mouse and Rabbit Specific HRP/DAB Detection IHC Kit) to quench endogenous peroxidase activity. After two washes in Tween 20-PBS, 2 min each, an antigen retrieval step was performed to break the protein cross-links and therefore to unmask the antigens and epitopes in formalin-fixed and paraffin embedded tissue sections, thus enhancing staining intensity of antibodies, with 0.05% trypsin (v/w) and 0.1% Calcium Chloride (v/w) in distilled water, by 20 min incubation at 37° C. After 10 min at room temperature to cool down samples, sections were washed twice in Tween 20-PBS, 2 min each, and incubated with protein blocking serum (Mouse and Rabbit Specific HRP/DAB Detection IHC Kit) for 10 min to avoid non-specific staining. After this, samples were incubated for 2 hours with primary antibodies diluted in 1% bovine albumin serum, as above. Then sections were washed 3 times in Tween 20-PBS, 2 min each, and incubated for 10 min with a biotinylated secondary antibody (Mouse and Rabbit Specific HRP/DAB Detection IHC Kit). After 3 more washes with Tween 20-PBS and samples were incubated with streptavidin (Mouse and Rabbit Specific HRP/DAB Detection IHC Kit) for another 10 min. After 3 more washes in Tween 20-PBS, 2 min each, samples were incubated with a DAB chromogen (Mouse and Rabbit Specific HRP/DAB Detection IHC Kit) for another 10 min for brown staining being developed. Samples were then washed 2 more times with Tween 20-PBS, 2 min each. Samples were counterstained with Harris haematoxylin for 3 seconds and excess staining was eliminated by several washes in distilled water. Finally, samples were dehydrated again for 10 min in 95% alcohol, followed by 2 changes in 100% alcohol of 2 min each. Samples were cleaned by 2 changes of xylene, 2 min each, and were mounted with a coverslip using DPX mounting medium. Controls consisted of samples incubated without primary and secondary antibodies, or incubated only with secondary antibodies.

Semi-quantitative assessment of the extent of immunostaining was performed on a blinded observer basis using a qualitative grading scale; absent=0, mild presence=1, large presence=2, abundance=3, great abundance=4. Five representative images from 2 representative samples at each time point were assessed by three blinded researchers (n=30). Example photographs depicting 0, 1, 2, 3 and 4 were provided for reference and the median value from these scores was used. The M2/M1 ratio was also calculated for each group using the values from the blind scoring of the immunostaining.

Statistics

Differences in the different staining were tested for statistical significance with a GraphPad Prism 8 software considering both factors together (group and implantation site) using a two-way ANOVA test and doing multiple comparisons between individual groups using a Sidak's test.

Results

Figure 14:
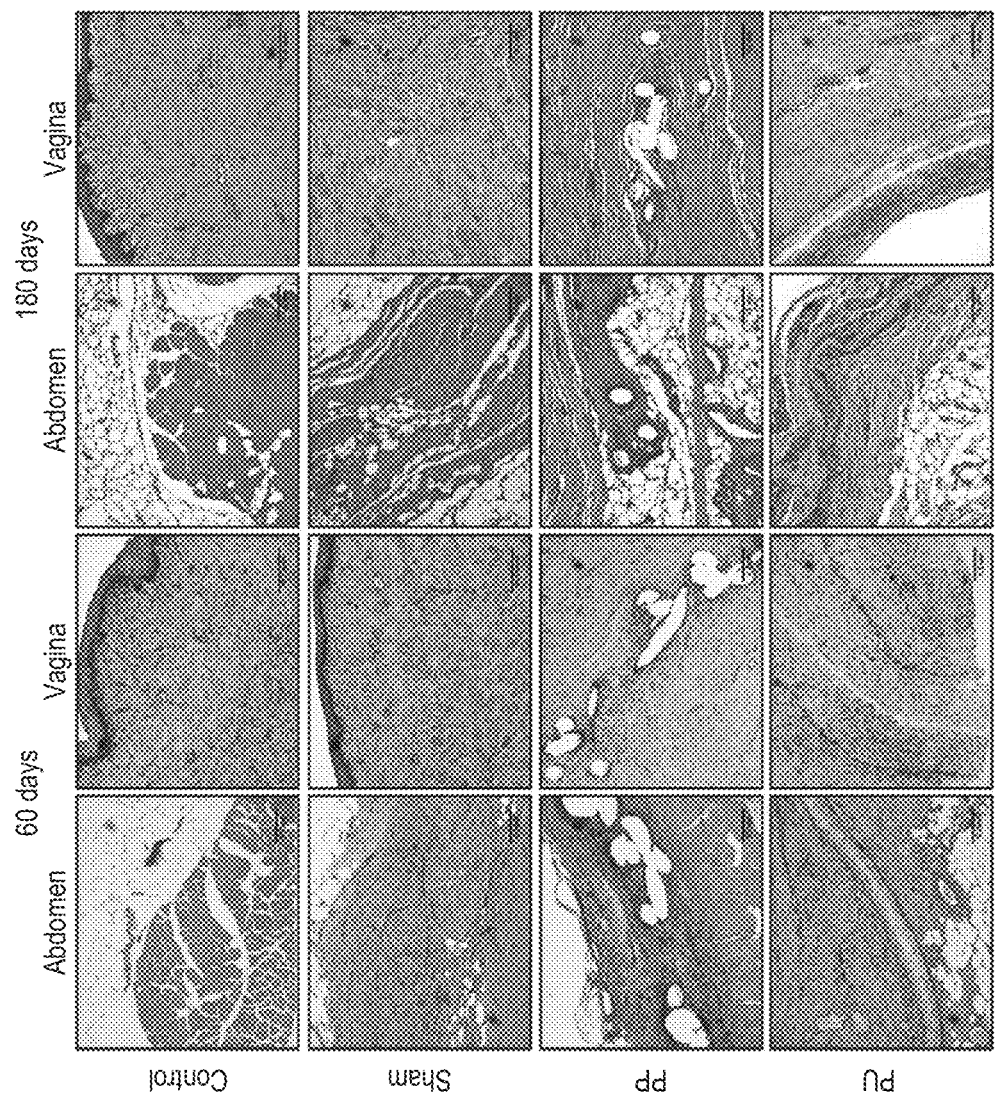
FIG. 14 shows H+E staining of abdominal and vaginal wall implants at 60 and 180 days. 100× magnification. Scale bar=0.2 mm.
Figure 15:
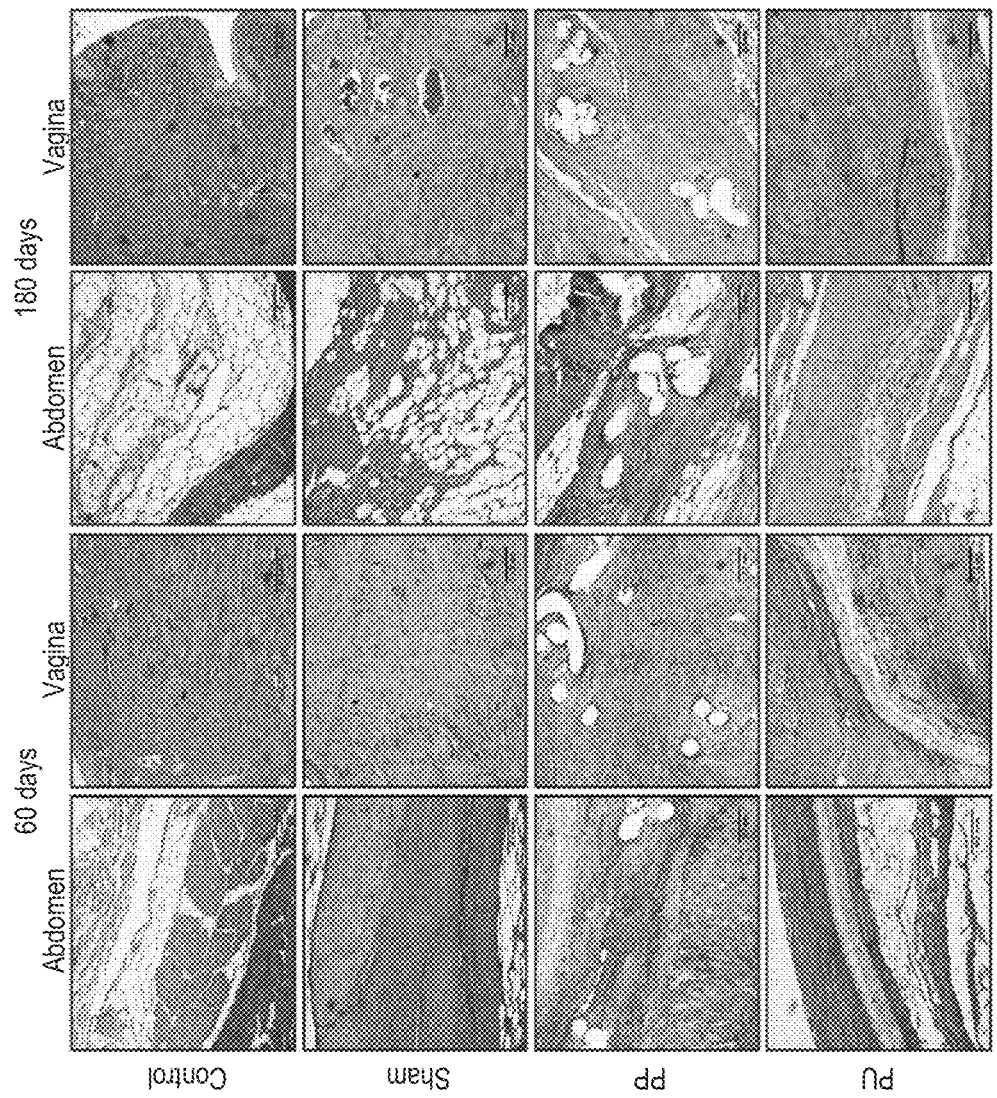
FIG. 15 shows Masson-Goldner trichrome staining of abdominal and vaginal wall implants at 60 and 180 days. 100× magnification. Scale bar=0.2 mm.
Figure 16:
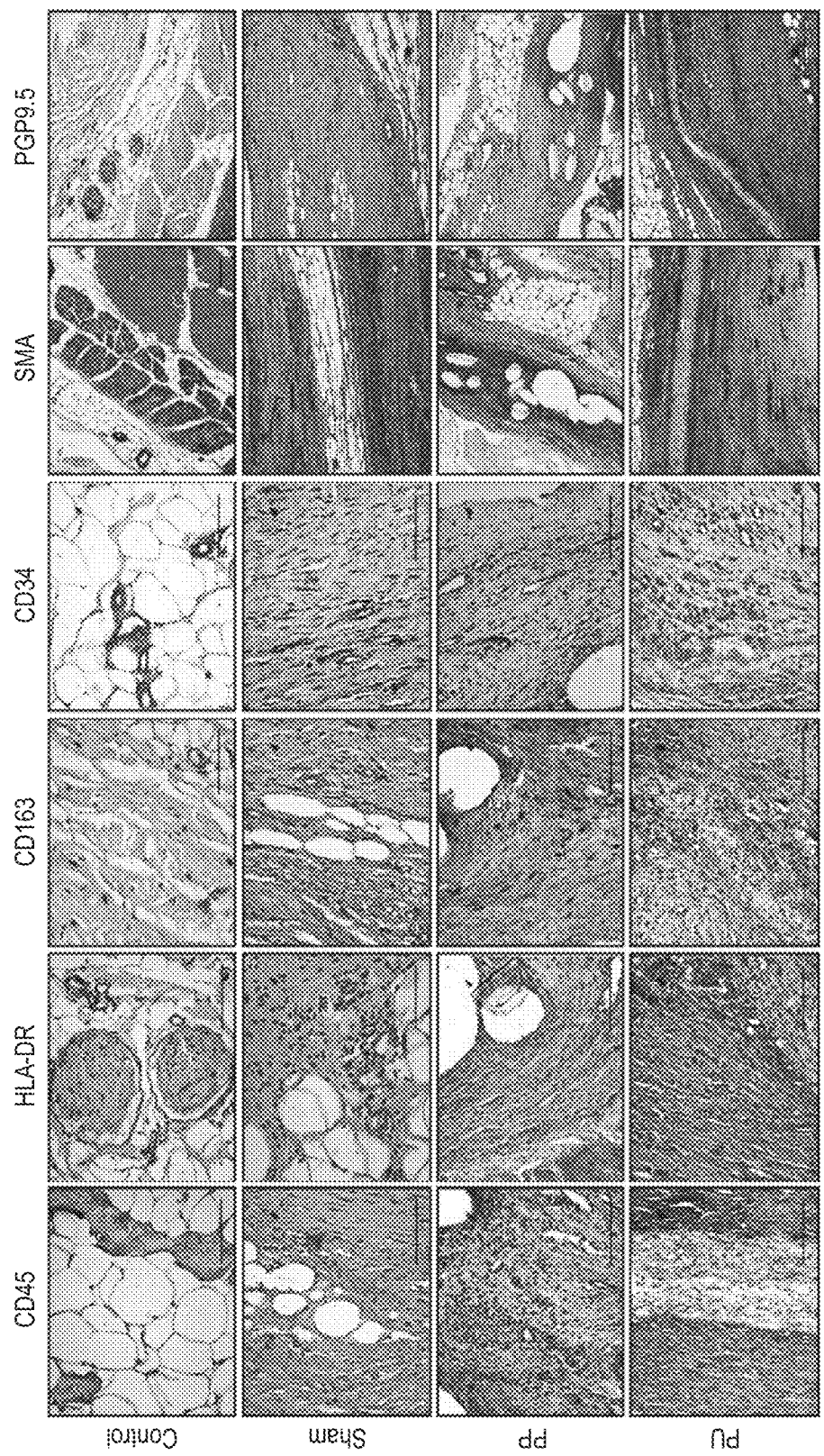
FIG. 16 shows immunohistochemistry staining of abdominal wall implants at 60 days for 6 different antibodies. 400× magnification, scale bar=0.1 for CD45, HLA-DR, CD163 and CD34. 100× magnification, scale bar=0.2 for smooth muscle actin (SMA) and PGP9.5.
Figure 17:
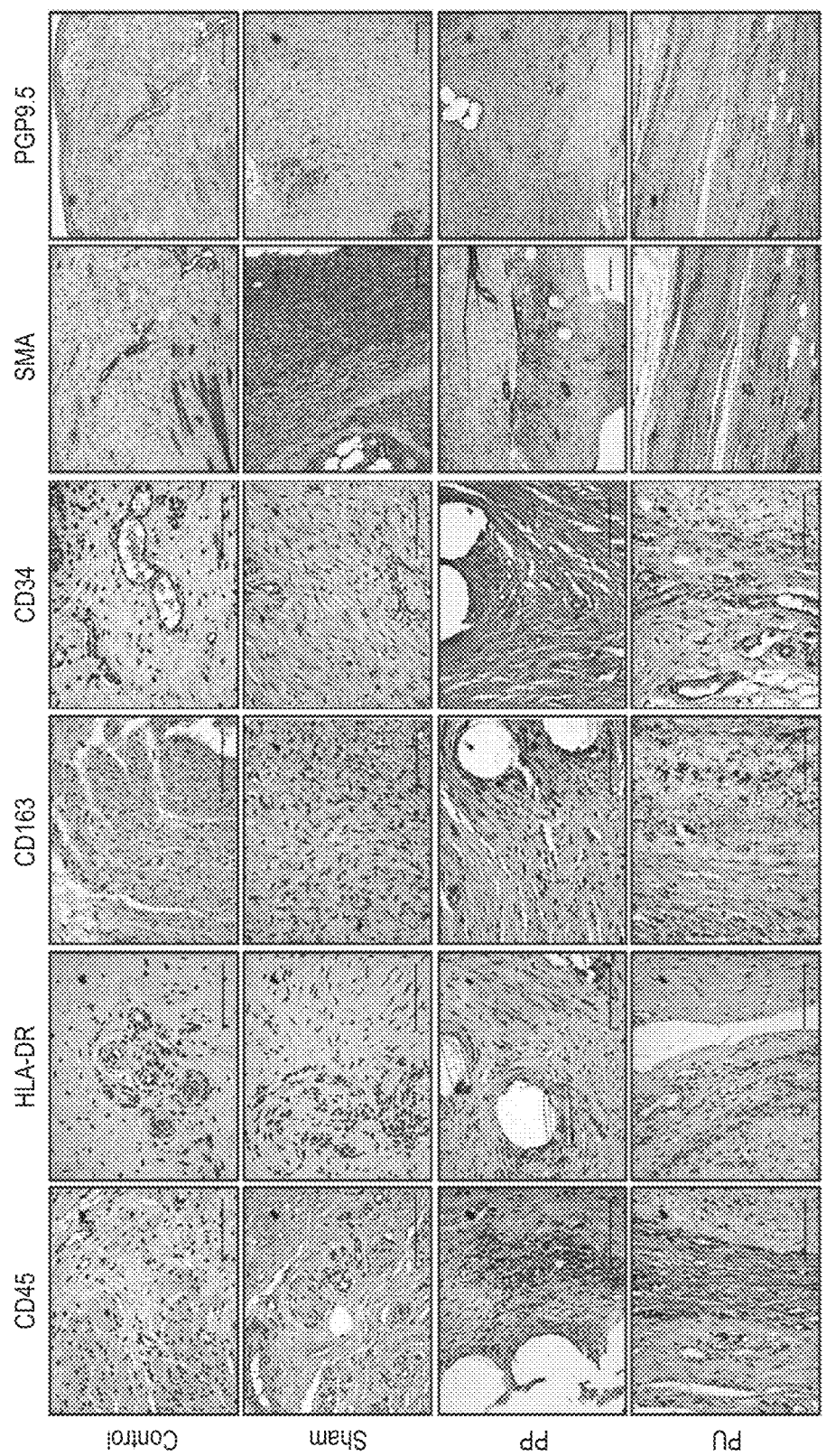
FIG. 17 shows immunohistochemistry staining of vaginal wall implants at 60 days for 6 different antibodies. 400× magnification, scale bar=0.1 for CD45, HLA-DR, CD163 and CD34. 100× magnification, scale bar=0.2 for smooth muscle actin (SMA) and PGP9.5.
Figure 18:
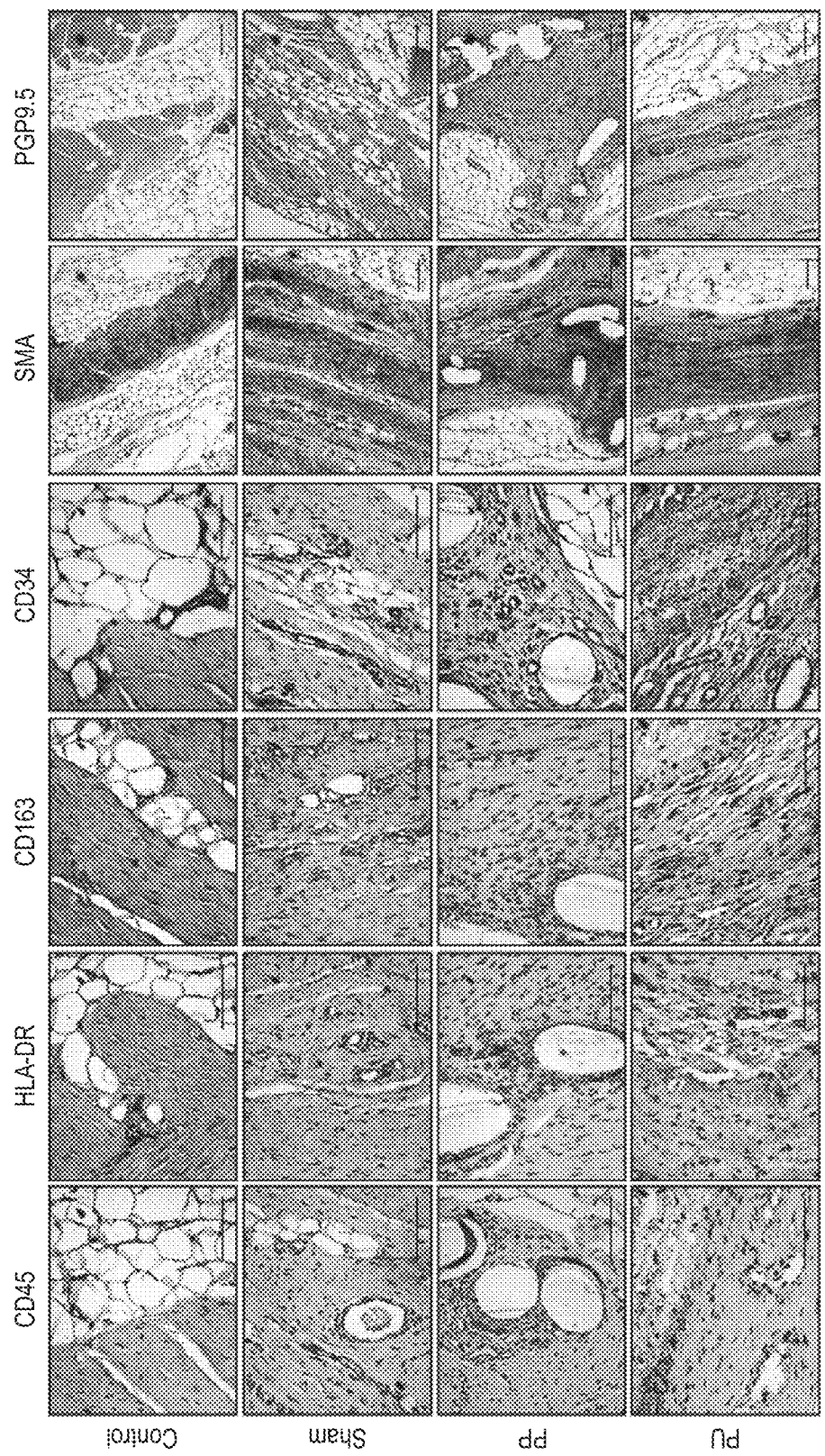
FIG. 18 shows immunohistochemistry staining of abdominal wall implants at 180 days for 6 different antibodies. 400× magnification, scale bar=0.1 for CD45, HLA-DR, CD163 and CD34. 100× magnification, scale bar=0.2 for smooth muscle actin (SMA) and PGP9.5.
Figure 19:
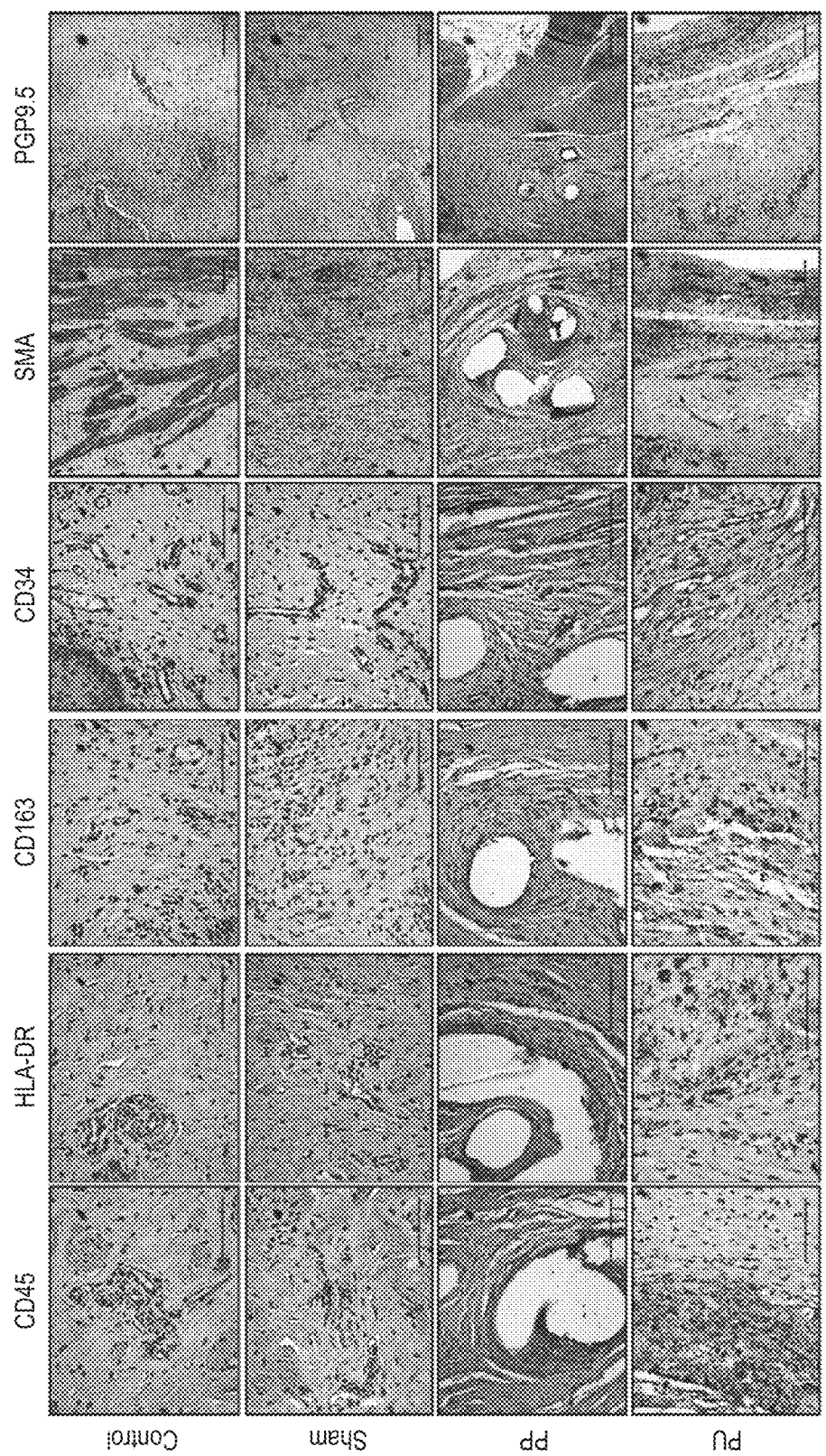
FIG. 19 shows immunohistochemistry staining of vaginal wall implants at 180 days for 6 different antibodies. 400× magnification, scale bar=0.1 for CD45, HLA-DR, CD163 and CD34. 100× magnification, scale bar=0.2 for smooth muscle actin (SMA) and PGP9.5.

FIG. 14 (H+E staining) and FIG. 15 (Masson-Goldner trichrome staining) show integration of PP meshes and tri-layer PU scaffolds within abdominal and vaginal tissues at 60 and 180 days. Whist a strong host cell response around the macro-filaments of the PP meshes can be been, there is a large cell infiltration within the tri-layer PU scaffolds with new blood vessels formed within the synthetic material. At 180 days it can still been seen that the 3 layer structure of the PU scaffolds with the aligned layer of fibres in the middle act as a barrier which cells cannot penetrate. There is a lot of new tissue formation around and between the microfilaments of the PP meshes similar to the new tissue formed at both sides of the tri-layer PU scaffolds; however, the tissue formed in the last group seems to be better organized specially within the vagina.

Figure 20:
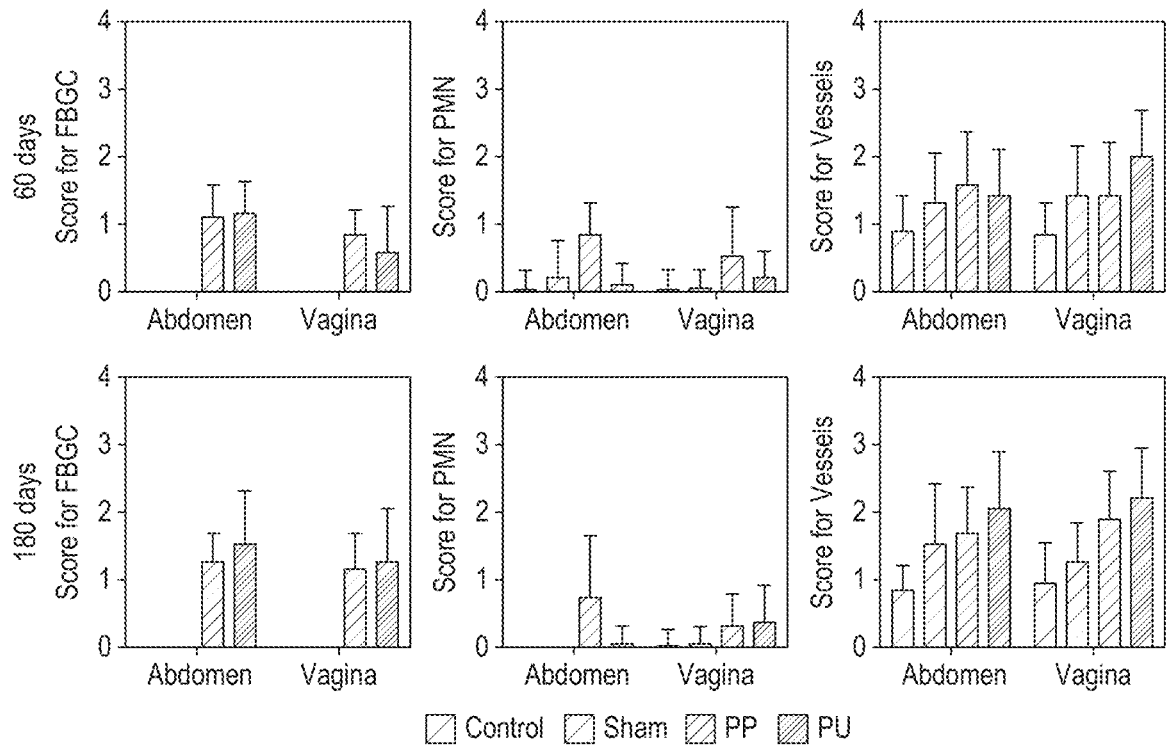
FIG. 20 shows graphs and a table of the semi-quantitative scoring of the H&E data. A score of 0-3 was used for all where 0=none and 3=extensive.

FIG. 20 (semi-quantitative scoring of the H&E data, of FIG. 14) shows a similar number of foreign body giant cells (FBGC) between PP meshes and tri-layer PU scaffolds, which was null for the control and sham. The number of polymorphonuclear cells (PMN) was higher for PP compared to all the other groups, but only within the abdomen. This may indicate a higher risk of infection when using PP meshes. Similar vascularity was measured between materials which was higher than controls in both tissues at both time points, and also higher than sham within the vagina at 180 days.

Figure 21:
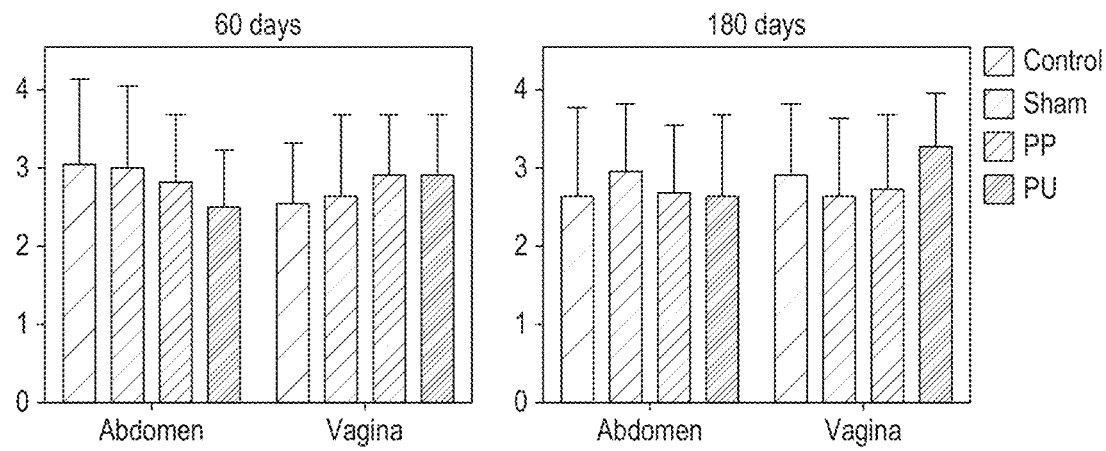
FIG. 21 shows graphs and table of the semi-quantitative scoring of the trichrome data. A score of 0-4 was used for all where 0=none and 4=great abundance.

FIG. 21 (semi-quantitative scoring of the Masson-Goldner trichrome data of FIG. 15) shows similar values of trichrome staining for all groups in both implant sites, suggesting similar collagen/connective tissue form surrounding the materials.

Figure 22:
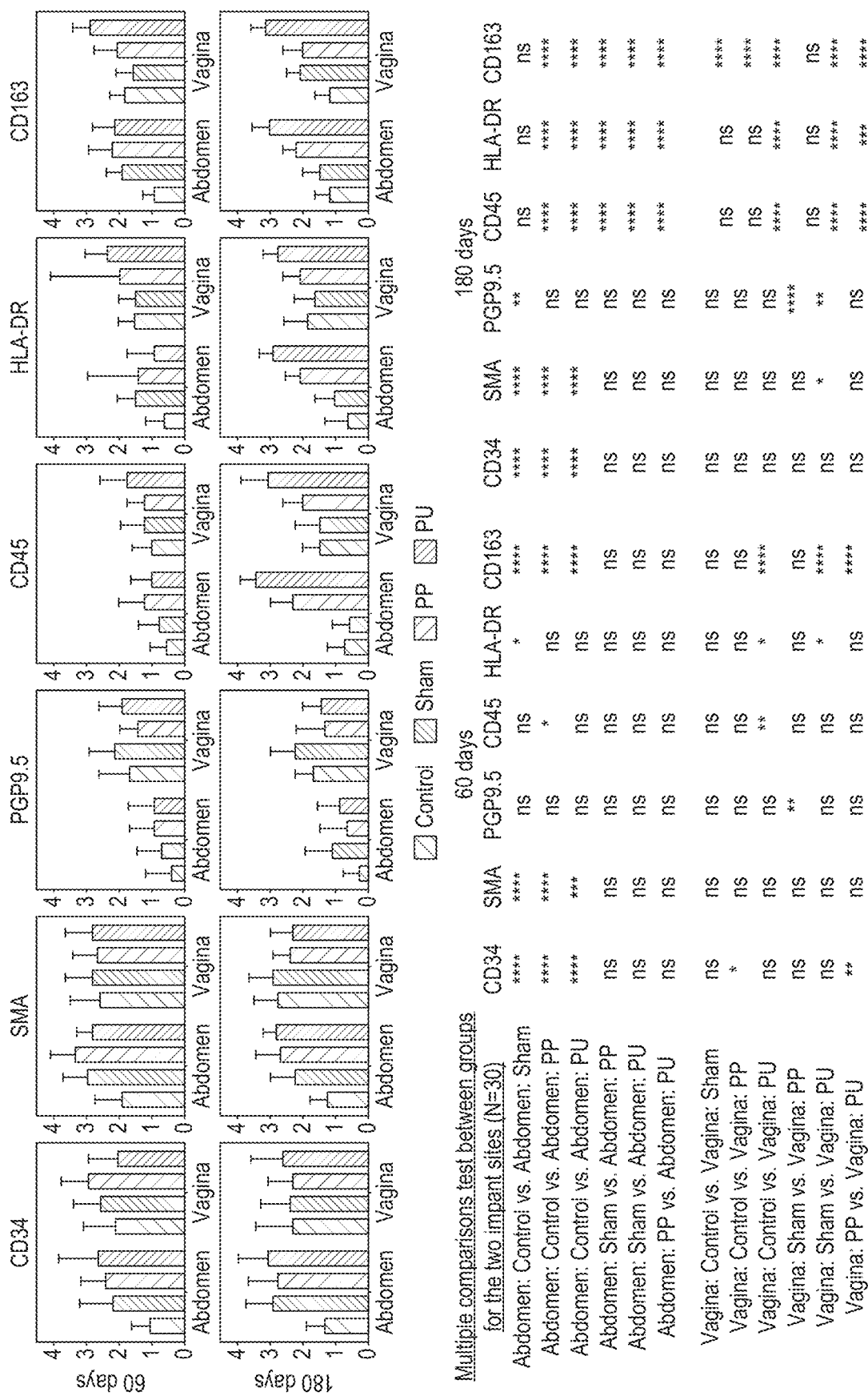
FIG. 22 shows graphs and a table of the semi-quantitative scoring of the IHC data (A score of 0-4 was used for all where 0=none and 4=great abundance).

FIG. 22 (semi-quantitative scoring of the IHC data of FIGS. 16-19) shows a similar vascularization between materials, as demonstrated by the CD34 staining, with higher values than the control group only visible within the abdomen at 180 days. Similar to trichrome staining, there was a similar smooth muscle actin (SMA) staining for all groups, which was again only lower for the control group at 180 days within the abdomen. There was a similar nerve (PGP9.5) staining between all groups, being slightly higher for the sham group within the vagina. In conclusion, both materials stimulate regeneration of a functional new connective tissue similar to the tissue formed by the normal wound healing represented by the sham group, with neo-vascularization, new collagenous matrix and new innervation respectively.

Figure 23:
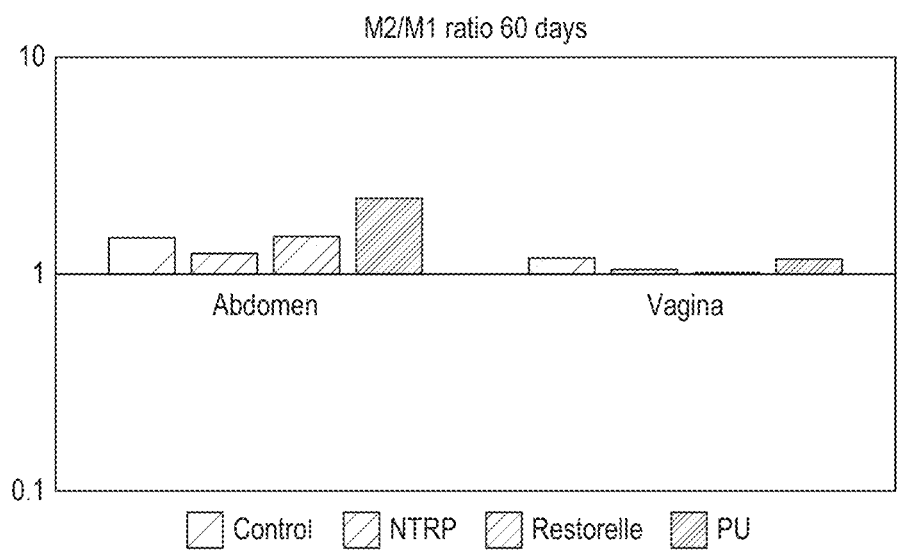
FIG. 23 shows the M2/M1 ratios for 60 and 180 days of abdomen and vagina implants. These were calculated for each group using the values from the blind scoring of the immunostaining, where the M1 response is the HLA-DR staining and the M2 response the D163 staining.
Figure 23:
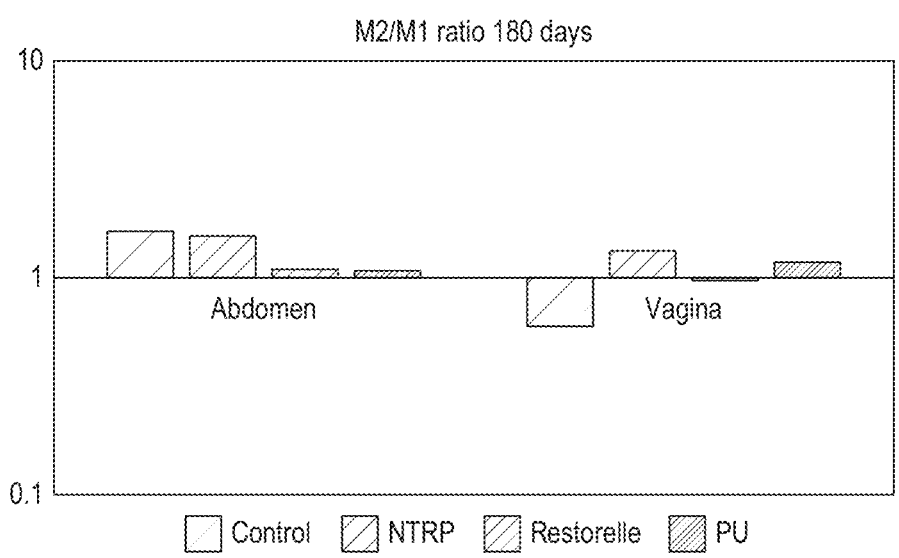

In terms of host/inflammatory response, FIG. 22 shows that while the lymphocyte (CD45) staining was much higher for both materials than the control and sham groups at 180 days within the abdomen, only the tri-layer PU scaffolds had higher values than the other groups within the vagina at 180 days. Same results were found for the M1 response (HLA-DR staining), with a higher values at 180 days for both materials than the control and sham groups within the abdomen but only for the tri-layer PU scaffolds within the vagina. Again, the M2 response (CD163 staining) was higher for both materials at 180 days within the abdomen compared to control and sham groups, but only for the tri-layer PU scaffolds within the vagina. The results suggest, as expected, a higher host response against the materials, although the response against PP meshes seems to be a bit lower and similar to the sham group within the vagina. Nevertheless, looking at the M2/M1 ratio (FIG. 23), it is positive and similar for both materials at 180 days within the abdomen, while this ratio is only positive for the tri-layer PU scaffolds within the vagina at 180 days, being similar to the sham group and being negative for the PP meshes more related to rejection with a chronic inflammatory response. Alternative the positive ratio for the tri-layer PU scaffolds suggest better integration with reconstructive remodelling.

REFERENCES

Mangera A, Bullock A J, Chapple C R, MacNeil S. Are biomechanical properties predictive of the success of prostheses used in stress urinary incontinence and pelvic organ prolapse? A systematic review. Neurourology and Urodynamics 31(1):13-21 (2012).

Hillary C J, Roman S, Bullock A J, Green N H, Chapple C R, MacNeil S. Developing repair materials for stress urinary incontinence to withstand dynamic distension. PLoS ONE, 2016, 11(3): e0149971.

Roman S, Urbánková I, Callewaert G, Lesage F, Hillary C, Osman N I, Chapple C R, Deprest J, MacNeil S. Evaluating alternative materials for the treatment of stress urinary incontinence and pelvic organ prolapse—a comparison of the in vivo response to meshes of polypropylene, polyvinylidene fluoride, poly-lactic acid and polyurethane implanted in rabbits for 3 months. The Journal of Urology, 2016, 196(1):261-269.

Bye F J, Bissola J, Black L, Bullock A J, Puwanun S, Moharamzadeh K, Reilly G C, Ryan A J, MacNeil S. Development of bilayer and trilayer nanofibrous/microfibrous scaffolds for regenerative medicine. Biomater. Sci. 2013, 1:942-951.

Lei L, Song Y, Chen R. Biomechanical properties of prolapsed vaginal tissue in pre- and postmenopausal women. Int Urogynecol J Pelvic Floor Dysfunct., 2007, June; 18(6):603-7.

Aboushwareb T, McKenzie P, Wezel F, Southgate J, Badlani G. Is tissue engineering and biomaterials the future for lower urinary tract dysfunction (LUTD)/pelvic organ prolapse (POP)? Neurourology and urodynamics. 2011; 30(5):775-82.

Badylak S F, Valentin J E, Ravindra A K, McCabe G P, Stewart-Akers A M. Macrophage phenotype as a determinant of biologic scaffold remodeling. Tissue engineering Part A. 2008; 14(11):1835-42.

Mantovani A, Sica A, Locati M. Macrophage polarization comes of age. Immunity. 2005; 23(4):344-6.

Claerhout F, Verbist G, Verbeken E, Konstantinovic M, De Ridder D, Deprest J. Fate of collagen-based implants used in pelvic floor surgery: a 2-year follow-up study in a rabbit model. American journal of obstetrics and gynecology. 2008; 198(1):94 e1-6.

Kowalczyk T., Nowicka A., Elbaum D., Kowalewski T., Electrospinning of Bovine Serum Albumin. Optimization and the Use for Production of Biosensors. Biomacromolecules. 2008 July; 9(7):2087-90;

Haliloglu, B., Karateke A., Coksuer H., Peker H., Cam C., The role of urethral hypermobility and intrinsic sphincteric deficiency on the outcome of transobturator tape procedure: a prospective study with 2-year follow-up, International Urogynecology Journal. 2010, 21(2), 173-178.

Toosie K, Gallego K, Stabile B E, Schaber B, French S, de Virgilio C. Fibrin glue reduces intra-abdominal adhesions to synthetic mesh in a rat ventral hernia model. Am Surg. 2000 January; 66(1):41-5.

Hong N, Yang G H, Lee J, Kim G. 3D bioprinting and its in vivo applications. J Biomed Mater Res B Appl Biomater. 2018, 106(1):444-459.

The invention claimed is:

1. A scaffold for treatment of stress urinary incontinence, wherein the scaffold comprises a first, second and third layer of polyurethane, wherein the first layer and the third layer comprise polyurethane fibres that are randomly orientated, and wherein the second layer is between said first and third layers, and wherein the second layer comprises polyurethane fibres that are aligned longitudinally; wherein the first and/or the third layer comprise pores, and wherein the pores have a mean pore diameter in the first and/or the third layer of at least 10 μm.

2. The scaffold in accordance with claim 1, in which the polyurethane is polyurethane Z3 or a polyether and polycarbonate based medical grade material.

3. The scaffold in accordance with claim 1, wherein the scaffold has an ultimate tensile strength of between 0.25 and 1.5 megapascal (MPa).

4. The scaffold in accordance with claim 1, wherein the scaffold has a strain at ultimate tensile strength of between 70% and 80%.

5. The scaffold in accordance with claim 1, wherein at least 20% of the pores on the outer surface of the first and/or third layer are greater than 18 micrometres (μm) in diameter and/or wherein at least 5% of the pores on the outer surface of the first and/or third layer are greater than 20 μm in diameter.

6. The scaffold in accordance with claim 1, wherein the pores are from the outermost surface of the scaffold to a depth of at least 8 um to 20 um suitable for penetration by human adipose derived mesenchymal stem cells.

7. A method of preparing a scaffold for treatment of stress urinary incontinence, the method comprising:
   a. electrospinning a sacrificial layer of poly-lactic acid (PLA) onto a rotating surface, wherein the sacrificial layer comprises randomly orientated degradable polymer fibres that can be readily separated from the scaffold;
   b. electrospinning a first layer of polyurethane in which fibres are spun in random orientations;
   c. electrospinning a second layer polyurethane in which fibres are spun in aligned longitudinal orientation;
   d. electrospinning a third layer in which fibres are spun in random orientations; and
   e. removing the sacrificial layer of PLA to produce the scaffold, wherein the electrospinning of the first and/or the third layer is performed in a manner that forms pores within the first and/or the third layer, wherein the pores from the outermost surface of the scaffold have a depth of at least 8 μm to 20 μm.

8. The method according to claim 7, wherein the method comprises use of at least two separate syringe pumps, one delivering random fibres and one delivering aligned fibres.

9. The method according to claim 7, wherein step c starts before step b finishes in a manner that there is an overlap between the first and second layer.

10. The method according to claim 7, wherein step d starts before step c finishes in a manner that there is an overlap between the second and third layer.

11. The method according to claim 7, wherein the sacrificial layer is applied to a surface rotating from 200 to 400 rotation per minute (rpm).

12. The method according to claim 7, wherein the sacrificial layer is produced with a needle to surface distance of from 12 cm to 17 centimetre (cm).

13. The method according to claim 7, wherein the sacrificial layer is produced by delivering polymer solutions at a rate of from 30 microliter per minute (μl/min) to 40 μl/min per syringe with an accelerating voltage of from 15 kilovolts (kV) to 19 kV direct current (DC).

14. The method according to claim 7, wherein step b is conducted after any excess solvent from step a. have evaporated.

15. The method according to claim 7, wherein the first and third layers are applied to a surface rotating from 200 to 400 rpm.

16. The method according to claim 7, wherein the first and third layers are produced with a needle to surface distance of from 12 to 17 cm and/or the second layer is produced by a needle to surface distance of from 5 cm to 10 cm.

17. The method according to claim 7, wherein the first and/or third layer is produced by delivering polymer solutions at a rate of from 30 μl/min per syringe to 40 μl/min per syringe with an accelerating voltage of from 17 kV DC to 23 kV DC.

18. The method according to claim 7, wherein the second layer is applied to a surface rotating from 500 to 700 rpm.

19. The method according to claim 7, wherein the second layer is produced by delivering polymer solutions at a rate of from 30 μl/min per syringe to 40 μl/min per syringe with a voltage of from 21 kV DC to 25 kV DC.

20. The scaffold produced by the method of claim 7.

* * * * *